(12) United States Patent
Cottard et al.

(10) Patent No.: US 7,364,594 B2
(45) Date of Patent: Apr. 29, 2008

(54) DYEING COMPOSITION FOR KERATINOUS FIBRES COMPRISING AN ASSOCIATIVE POLYMER AND A POLYMER WITH ACRYLAMIDE UNITS, DIALKYLDIALLYLAMMONIUM HALIDE, AND VINYLIC CARBOXYLIC ACID

(75) Inventors: François Cottard, Levallois-Perret (FR); Christine Rondeau, Sartrouville (FR)

(73) Assignee: L'Oreal S.A., Paris (FR)

( * ) Notice: Subject to any disclaimer, the term of this patent is extended or adjusted under 35 U.S.C. 154(b) by 100 days.

(21) Appl. No.: 10/433,506

(22) PCT Filed: Nov. 22, 2001

(86) PCT No.: PCT/FR01/03693

§ 371 (c)(1),
(2), (4) Date: Oct. 24, 2003

(87) PCT Pub. No.: WO02/45674

PCT Pub. Date: Jun. 13, 2002

(65) Prior Publication Data

US 2004/0060126 A1   Apr. 1, 2004

(30) Foreign Application Priority Data

Dec. 4, 2000   (FR)   .................... 00 15682

(51) Int. Cl.
*A61K 7/13* (2006.01)
(52) U.S. Cl. .................. 8/405; 8/406; 8/409; 8/410; 8/421; 8/435; 8/552; 8/554
(58) Field of Classification Search .................. 8/405, 8/409, 410, 421, 435, 552, 554, 406
See application file for complete search history.

(56) References Cited

U.S. PATENT DOCUMENTS

| | | | |
|---|---|---|---|
| 2,261,002 A | 10/1941 | Ritter | 260/570 |
| 2,271,378 A | 1/1942 | Searle | 167/22 |
| 2,273,780 A | 2/1942 | Dittmar | 260/28 |
| 2,375,853 A | 5/1945 | Kirby et al. | 260/583 |
| 2,388,614 A | 11/1945 | Kirby et al. | 167/22 |
| 2,454,547 A | 11/1948 | Bock et al. | 260/567.6 |
| 2,528,378 A | 10/1950 | Mannheimer | 265/309.6 |
| 2,781,354 A | 2/1957 | Mannheimer | 260/309.6 |
| 2,961,347 A | 11/1960 | Floyd | 117/141 |
| 3,206,462 A | 9/1965 | McCarty | 260/256.4 |
| 3,227,615 A | 1/1966 | Korden | 167/87.1 |
| 3,472,840 A | 10/1969 | Stone et al. | 260/231 |
| 3,632,559 A | 1/1972 | Matter et al. | 260/78 |
| 3,836,537 A | 9/1974 | Boerwinkle et al. | 260/29.6 |
| 3,874,870 A | 4/1975 | Green et al. | 71/67 |
| 3,879,376 A | 4/1975 | Vanlerberghe et al. | 260/211 |
| 3,912,808 A | 10/1975 | Sokol | 424/71 |
| 3,915,921 A | 10/1975 | Schlatzer, Jr. et al. | 260/17.11 |
| 3,917,817 A | 11/1975 | Vanlerberghe et al. | 424/70 |
| 3,929,990 A | 12/1975 | Green et al. | 424/78 |
| 3,966,904 A | 6/1976 | Green et al. | 424/78 |
| 3,986,825 A | 10/1976 | Sokol | 8/10.1 |
| 4,001,432 A | 1/1977 | Green et al. | |
| 4,003,699 A | 1/1977 | Rose et al. | 8/10.2 |
| 4,005,193 A | 1/1977 | Green et al. | 474/168 |
| 4,013,787 A | 3/1977 | Varlerberghe et al. | 424/70 |
| 4,025,617 A | 5/1977 | Green et al. | 424/78 |
| 4,025,627 A | 5/1977 | Green et al. | 424/248.4 |
| 4,025,653 A | 5/1977 | Green et al. | 424/325 |
| 4,026,945 A | 5/1977 | Green et al. | 260/567.6 |
| 4,027,020 A | 5/1977 | Green et al. | 424/248.56 |
| 4,031,307 A | 6/1977 | DeMartino et al. | 536/114 |
| 4,075,136 A | 2/1978 | Schaper | 260/2 |
| 4,131,576 A | 12/1978 | Iovine et al. | 260/17.4 |
| 4,157,388 A | 6/1979 | Christiansen | 424/70 |
| 4,166,894 A | 9/1979 | Schaper | 528/271 |
| 4,172,887 A | 10/1979 | Vanlerberghe et al. | 424/70 |
| 4,223,009 A | 9/1980 | Chakrabarti | 424/47 |
| 4,240,450 A | 12/1980 | Grollier et al. | 132/7 |
| 4,277,581 A | 7/1981 | Vanlerberghe et al. | 525/420 |
| 4,349,532 A | 9/1982 | Vanlerberghe et al. | 424/47 |
| 4,381,919 A | 5/1983 | Jacquet et al. | 8/405 |
| 4,509,949 A | 4/1985 | Huang et al. | 586/558 |

(Continued)

FOREIGN PATENT DOCUMENTS

DE      23 59 399       6/1975

(Continued)

OTHER PUBLICATIONS

English language Derwent Abstract of DE 19 905 615, Aug. 17, 2000.

(Continued)

*Primary Examiner*—Eisa Elhilo
(74) *Attorney, Agent, or Firm*—Finnegan, Henderson, Farabow, Garrett & Dunner, L.L.P.

(57) ABSTRACT

The invention concerns a composition for dyeing and in particular oxidation dyeing of keratinous fibers, in particular human keratinous fibers and more particularly hair, comprising, in a medium suitable for dyeing, at least an oxidation dye and/or a direct dye and at least an associative polymer, characterised in that it further comprises a polymer with acrylamide units (i), (ii) dialkyldiallylammonium halide, and (iii) vinylic carboxylic acid. The invention also concerns dyeing methods and devices using said dyeing composition.

45 Claims, No Drawings

U.S. PATENT DOCUMENTS

| | | | |
|---|---|---|---|
| 4,591,610 A | 5/1986 | Grollier | 524/55 |
| 4,702,906 A | 10/1987 | Jacquet et al. | 424/70 |
| 4,719,282 A | 1/1988 | Nadolsky et al. | 528/310 |
| 4,761,273 A | 8/1988 | Grollier et al. | 424/47 |
| 4,839,166 A | 6/1989 | Grollier et al. | 424/71 |
| 4,996,059 A | 2/1991 | Grollier et al. | 424/71 |
| 5,061,289 A | 10/1991 | Clausen et al. | 252/49.3 |
| 5,089,252 A | 2/1992 | Grollier et al. | 424/4.7 |
| 5,196,189 A | 3/1993 | Jacquet et al. | 424/72 |
| 5,380,340 A | 1/1995 | Neunhoeffer et al. | 8/409 |
| 5,534,267 A | 7/1996 | Neunhoeffer et al. | 424/70.1 |
| 5,663,366 A | 9/1997 | Neunhoeffer et al. | 548/371.4 |
| 5,735,908 A * | 4/1998 | Cotteret et al. | 8/410 |
| 5,766,576 A | 6/1998 | Lowe et al. | 424/62 |
| 5,876,463 A | 3/1999 | Garcia et al. | 8/405 |
| 5,879,412 A * | 3/1999 | Rondeau et al. | 8/411 |
| 5,976,517 A * | 11/1999 | Dubief et al. | 424/70.1 |
| 6,099,592 A | 8/2000 | Vidal et al. | 8/409 |
| 6,099,593 A | 8/2000 | Terranova et al. | 8/409 |
| 6,156,076 A * | 12/2000 | Casperson et al. | 8/406 |
| 6,284,003 B1 | 9/2001 | Rose et al. | 8/412 |
| 6,423,101 B1 | 7/2002 | Yaker et al. | 8/405 |
| 6,432,146 B1 | 8/2002 | Rondeau | 8/407 |
| 6,530,959 B1 | 3/2003 | Lang et al. | 8/405 |
| 2001/0023515 A1* | 9/2001 | Cottard et al. | 8/406 |
| 2004/0141943 A1 | 7/2004 | Mougin et al. | 424/70.17 |
| 2005/0071933 A1 | 4/2005 | Rondeau | 8/405 |

FOREIGN PATENT DOCUMENTS

| | | |
|---|---|---|
| DE | 195 43 988 | 5/1977 |
| DE | 38 43 892 | 6/1990 |
| DE | 41 33 957 | 4/1993 |
| DE | 199 05 615 | 8/2000 |
| EP | 0 080 976 | 6/1983 |
| EP | 0 122 324 | 10/1984 |
| EP | 0 173 109 | 3/1986 |
| EP | 0 216 479 | 4/1987 |
| EP | 0 337 354 | 10/1989 |
| EP | 1 025 834 | 8/2000 |
| FR | 1 400 366 | 5/1963 |
| FR | 1 492 597 | 9/1966 |
| FR | 1 583 363 | 10/1969 |
| FR | 2 077 143 | 10/1971 |
| FR | 2 080 759 | 11/1971 |
| FR | 2 137 684 | 12/1972 |
| FR | 2 162 025 | 7/1973 |
| FR | 2 190 406 | 2/1974 |
| FR | 2 252 840 | 6/1975 |
| FR | 2 270 846 | 12/1975 |
| FR | 2 280 361 | 2/1976 |
| FR | 2 316 271 | 1/1977 |
| FR | 2 320 330 | 3/1977 |
| FR | 2 336 434 | 7/1977 |
| FR | 2 368 508 | 5/1978 |
| FR | 2 383 660 | 10/1978 |
| FR | 2 393 573 | 1/1979 |
| FR | 2 413 907 | 8/1979 |
| FR | 2 470 596 | 6/1981 |
| FR | 2 505 348 | 11/1982 |
| FR | 2 519 863 | 7/1983 |
| FR | 2 542 997 | 9/1984 |
| FR | 2 598 611 | 11/1987 |
| FR | 2 733 749 | 11/1996 |
| FR | 2 750 048 | 12/1997 |
| FR | 2 782 450 | 2/2000 |
| FR | 2 782 451 | 2/2000 |
| FR | 2 782 452 | 2/2000 |
| FR | 2 811 993 | 1/2002 |
| GB | 1021400 | 3/1966 |
| GB | 1026978 | 4/1966 |
| GB | 1153196 | 5/1969 |
| GB | 1546809 | 5/1979 |
| JP | 02 019576 | 1/1990 |
| JP | 09 110659 | 4/1997 |
| WO | WO-94/08969 | 4/1994 |
| WO | WO-94/08970 | 4/1994 |
| WO | WO-94/10968 | 5/1994 |
| WO | WO-96/15765 | 5/1996 |
| WO | WO-97/44002 | 11/1997 |
| WO | WO-98/44012 | 10/1998 |
| WO | WO-99/13822 | 3/1999 |
| WO | WO-99/36047 | 7/1999 |
| WO | WO-99/37278 | 7/1999 |

OTHER PUBLICATIONS

English language Derwent Abstract of EP 0 080 976, Jun. 8, 1983.
English language Derwent Abstract of FR 2 782 452, Feb. 25, 2000.
English language Japio Abstract of JP 02-019576, Jan. 23, 1990.
English language Japio Abstract of JP 09-110659, Apr. 28, 1997.
Fonnum, et al. "Associative Thickeners. Part I: Synthesis, Rheology and Aggregation Behavior", Colloid Polym Sci 271:380-389 (1993).
International Search Report of PCT/FR01/03693, Apr. 15, 2002.
Porter, M.R. Handbook of Surfactants, Blackie: Glaskow and London, 1991.

* cited by examiner

DYEING COMPOSITION FOR KERATINOUS FIBRES COMPRISING AN ASSOCIATIVE POLYMER AND A POLYMER WITH ACRYLAMIDE UNITS, DIALKYLDIALLYLAMMONIUM HALIDE, AND VINYLIC CARBOXYLIC ACID

FIELD OF THE INVENTION

The invention relates to a composition for the dyeing and especially for the oxidation dyeing of keratin fibers, in particular of human keratin fibers and more particularly the hair, comprising, in a medium that is suitable for dyeing, at least one oxidation dye and/or a direct dye and at least one associative polymer, and which is characterized in that it also comprises at least one polymer containing (i) acrylamide, (ii) dialkyldiallylammonium halide and (iii) vinylcarboxylic acid units.

The invention also relates to the dyeing devices and processes using said composition.

BACKGROUND OF THE INVENTION

In the hair sector, two types of dyeing may be distinguished.

The first is semi-permanent or temporary dyeing, or direct dyeing, which involves dyes that are capable of giving the natural coloration of the hair a more or less pronounced color change that may be resistant to shampoo-washing several times. These dyes are known as direct dyes; they may be used with or without an oxidizing agent. In the presence of an oxidizing agent, the aim is to obtain lightening direct dyeing. Lightening dyeing is carried out by applying to the hair an extemporaneous mixture of a direct dye and an oxidizing agent, which makes it possible especially to obtain, by lightening the melanin of the hair, an advantageous effect such as a uniform color in the case of gray hair, or to bring out the color in the case of naturally pigmented hair.

The second is permanent dyeing or oxidation dyeing. This is performed with "oxidation" dyes comprising oxidation dye precursors and couplers. Oxidation dye precursors, commonly called "oxidation bases", are compounds that are initially uncolored or only weakly colored, which develop their dyeing power on the hair in the presence of oxidizing agents that are added at the time of use, leading to the formation of colored and dyeing compounds. The formation of these colored and dyeing compounds results either from an oxidative condensation of the "oxidation bases" with themselves or from an oxidative condensation of the "oxidation bases" with coloration modifiers commonly called "couplers" and which are generally present in the dye compositions used in oxidation dyeing.

The variety of molecules used, which consist on the one hand of the "oxidation bases" and on the other hand of the "couplers", allows a very wide range of colors to be obtained.

To further vary the shades obtained with said oxidation dyes, or to enrich them with glints, direct dyes may be added thereto.

The "permanent" coloration obtained with these oxidation dyes must moreover satisfy a certain number of requirements. Thus, it must be able to produce shades in the desired intensity and must show good resistance to external agents (light, bad weather, washing, permanent-waving, perspiration and rubbing).

The dyes must also be able to cover gray hair, and, finally, they must be as unselective as possible, i.e. they must produce the smallest possible color differences along the same keratin fiber, which may in fact be differently sensitized (i.e. damaged) between its end and its root.

To localize the oxidation dye product to application to the hair, so that it does not run onto the face or beyond the areas that it is intended to dye, in addition to the use of conventional thickeners, such as crosslinked polyacrylic acid, hydroxyethylcelluloses, waxes, and mixtures of appropriately selected nonionic surfactants with an HLB (Hydrophilic-Lipophilic Balance) value, associative polymers of anionic, nonionic or cationic type have also been used.

Associative polymers of anionic, nonionic or cationic type represent a major advance in the search for a solution to this problem.

DETAILED DESCRIPTION OF THE INVENTION

The Applicant has now discovered, entirely surprisingly and unexpectedly, novel dye compositions that are optimal in terms of application to the fibers (they do not run, and thus remain better located at the point of application), in terms of obtaining powerful and chromatic shades with low selectivities and good staying power, and in terms of the cosmetic properties imparted to the treated hair, said dye compositions comprising in the dye composition, or in the oxidizing composition (when it is a lightening direct dye or oxidation dye), or in the two compositions simultaneously, besides at least one associative polymer, an effective amount of at least one polymer containing (i) acrylamide, (ii) dialkyldiallylammonium halide and (iii) vinylcarboxylic acid units.

This discovery forms the basis of the present invention.

One subject of the present invention is thus a novel composition for the dyeing of keratin fibers, in particular of human keratin fibers such as the hair, comprising, in a medium that is suitable for dyeing, at least one dye and at least one associative polymer, and which is characterized in that it also contains at least one polymer containing (i) acrylamide, (ii) dialkyldiallylammonium halide and (iii) vinylcarboxylic acid units.

According to the invention, said dye may be a direct dye or an oxidation dye (oxidation base and/or coupler).

Another subject of the present invention relates to a ready-to-use composition for the dyeing of keratin fibers, in particular of human keratin fibers such as the hair, comprising at least one dye (direct dye or oxidation dye), at least one associative polymer, at least one polymer containing (i) acrylamide, (ii) dialkyldiallylammonium halide and (iii) vinylcarboxylic acid units, and additionally at least one oxidizing agent.

For the purposes of the present invention, the expression "ready-to-use composition" means any composition intended to be applied immediately to the keratin fibers; it may thus be stored before use without further modification, or may result from the extemporaneous mixing of two or more compositions.

The invention is also directed toward a process for the dyeing of keratin fibers, and in particular of human keratin fibers such as the hair, which consists in applying to the fibers at least one dye composition comprising, in a medium that is suitable for dyeing, at least one dye (direct dye or oxidation dye), the color being developed at alkaline, neutral or acidic pH using an oxidizing composition containing at least one oxidizing agent, which is mixed with the dye composition just at the time of use or which is applied sequentially without intermediate rinsing, at least one associative polymer and at least one polymer containing (i) acrylamide, (ii) dialkyldiallylammonium halide and (iii) vinylcarboxylic acid units being present in the dye composition or in the oxidizing composition or in each of said compositions.

In a preferred process, the associative polymer(s) and the polymers containing (i) acrylamide, (ii) dialkyldiallylammonium halide and (iii) vinylcarboxylic acid units are present in the dye composition.

A subject of the invention is also multi-compartment dyeing devices or "kits".

A two-compartment device according to the invention comprises a compartment containing a dye composition comprising, in a medium that is suitable for dyeing, at least one dye (direct dye or oxidation dye), and another compartment containing an oxidizing composition comprising, in a medium that is suitable for dyeing, an oxidizing agent, at least one associative polymer and at least one polymer containing (i) acrylamide, (ii) dialkyldiallylammonium halide and (iii) vinylcarboxylic acid units being present in the dye composition or the oxidizing composition or in each of these compositions.

However, other characteristics, aspects, subjects and advantages of the invention will emerge even more clearly on reading the description and the examples that follow.

Polymers Containing (i) acrylamide, (ii) dialkyldiallylammonium halide and (iii) vinylcarboxylic Acid Units Used, According to the Invention According to the invention, the term "acrylamide units" is intended to denote units of structure (I):

$$H_2C=\underset{R_1}{\overset{}{C}}-\underset{O}{\overset{\|}{C}}-R_2 \quad (I)$$

in which:
R$_1$ denotes H or CH$_3$,
R$_2$ is chosen from an amino, dimethylamino, tert-butylamino, dodecylamino or —NH—CH$_2$OH radical.

The acrylamide unit [formula (I) in which R$_1$ is H and R$_2$ is amino] is particularly preferred.

The dialkyldiallylammonium halide units are of structure (II) below:

$$-(CH_2)t-C\underset{H_2C}{\overset{(CH_2)k}{R_5}}\underset{\underset{R_3\ R_4}{N^+}}{\overset{CH_2}{C(R_5)}}-CH_2- \quad (II)$$

in which formula k and t are equal to 0 or 1, the sum k+t being equal to 1; R$_5$ denotes a hydrogen atom or a methyl radical; R$_3$ and R$_4$, independently of each other, denote an alkyl group containing from 1 to 4 carbon atoms, a hydroxyalkyl group in which the alkyl group preferably contains 1 to 5 carbon atoms, an amido(C$_1$-C$_4$)alkyl group, or R$_3$ and R$_4$ may denote, together with the nitrogen atom to which they are attached, heterocyclic groups such as piperidyl or morpholinyl; R$_3$ and R$_4$, independently of each other, preferably denote an alkyl group containing from 1 to 4 carbon atoms; Y$^-$ is an anion such as bromide, chloride, acetate, borate, citrate, tartrate, bisulfate, bisulfite, sulfate or phosphate.

Among these dialkyldiallylammonium halide units, dimethyldiallylammonium chloride is preferred.

According to the invention, the term "vinylcarboxylic acid units" is also intended to denote acrylic acid, methacrylic acid and 2-acrylamido-2-methylpropanesulfonic acid.

The acrylic acid unit is particularly preferred.

Among these polymers containing (i) acrylamide, (ii) dialkyldiallylammonium halide and (iii) vinylcarboxylic acid units, mention may be made especially of the acrylamide/dimethyldiallylammonium chloride/acrylic acid terpolymers listed in the CTFA dictionary, International Cosmetic Ingredient Dictionary, 7th edition, 1997, under the name "Polyquaternium 39"; examples of such polymers have the following weight compositions:

(25/50/25), sold by the company Calgon,
under the name Merquat Plus 3330 Dry®,
as an aqueous 10% solution under the name Merquat Plus 3330®,
as an aqueous 23.6% solution under the name Polymer 3413-54,
as an aqueous 23.3% solution under the name Polymer 3413-58,
as an aqueous 21.3% solution under the name Polymer 3413-62,
(50/40/10), sold by the company Calgon,
as an aqueous 5% solution under the name Polymer 3120-59,
(50/35/15), sold by the company Calgon,
as an aqueous 5% solution under the name Polymer 3120-61,
(50/30/20), sold by the company Calgon,
as an aqueous 4.6% solution under the name Polymer 3120-63;

mention may also be made of the acrylamide/dimethyidiallylammonium chloride/2-acrylamido-2-methylpropanesulfonic acid terpolymer sold as an aqueous 8% solution by the company Calgon under the name Polymer 3575-53.

According to the invention, the polymer(s) containing (i) acrylamide, (ii) dialkyldiallylammonium halide and (iii) vinylcarboxylic acid units represent(s) about 0.1% to 10% by weight, preferably about 0.5% to 5% by weight and more particularly about 1% to 3% by weight relative to the total weight of the dye composition.

Associative Polymers Used According to the Invention

Associative polymers are water-soluble polymers capable, in an aqueous medium, of reversibly associating together or with other molecules.

Their chemical structure comprises hydrophilic zones and hydrophobic zones characterized by at least one fatty chain.

The associative polymers according to the invention may be of anionic, cationic or amphoteric type, and preferably of nonionic type.

Associative Polymers of Anionic Type:

Among these, mention may be made of:

(I) those comprising at least one hydrophilic unit and at least one fatty-chain allyl ether unit, more particularly those whose hydrophilic unit consists of an ethylenic unsaturated anionic monomer, more particularly a vinylcarboxylic acid and most particularly an acrylic acid or a methacrylic acid or mixtures thereof, the fatty-chain allyl ether unit of which corresponding to the monomer of formula (I) below:

$$CH_2=CR'CH_2OB_nR \quad (I)$$

in which R' denotes H or $CH_3$, B denotes an ethyleneoxy radical, n is zero or denotes an integer ranging from 1 to 100, R denotes a hydrocarbon-based radical chosen from alkyl, arylalkyl, aryl, alkylaryl and cycloalkyl radicals, containing from 8 to 30 carbon atoms, preferably 10 to 24 carbon atoms and even more particularly from 12 to 18 carbon atoms. A unit of formula (I) that is more particularly preferred is a unit in which R' denotes H, n is equal to 10 and R denotes a stearyl ($C_{18}$) radical.

Anionic associative polymers of this type are described and prepared, according to an emulsion polymerization process, in patent EP-0 216 479.

Among these anionic associative polymers that are particularly preferred according to the invention are polymers formed from 20% to 60% by weight of acrylic acid and/or of methacrylic acid, from 5% to 60% by weight of lower alkyl (meth)acrylates, from 2% to 50% by weight of fatty-chain allyl ether of formula (I), and from 0% to 1% by weight of a crosslinking agent which is a well-known copolymerizable unsaturated polyethylenic monomer, for instance diallyl phthalate, allyl (meth)acrylate, divinylbenzene, (poly)ethylene glycol dimethacrylate or methylenebisacrylamide.

Among the latter polymers, those most particularly preferred are crosslinked terpolymers of methacrylic acid, of ethyl acrylate and of polyethylene glycol (10 EO) stearyl ether (Steareth-10), in particular those sold by the company Allied Colloids under the names Salcare SC 80 and Salcare SC 90, which are aqueous 30% emulsions of a crosslinked terpolymer of methacrylic acid, of ethyl acrylate and of steareth-10 allyl ether (40/50/10).

(II) those comprising at least one hydrophilic unit of unsaturated olefinic carboxylic acid type, and at least one hydrophobic unit of ($C_{10}$-$C_{30}$)alkyl ester of unsaturated carboxylic acid type.

Preferably, these polymers are chosen from those in which the hydrophilic unit of unsaturated olefinic carboxylic acid type corresponds to the monomer of formula (II) below:

in which $R_1$ denotes H or $CH_3$ or $C_2H_5$, that is to say acrylic acid, methacrylic acid or ethacrylic acid units, and in which the hydrophobic unit of ($C_{10}$-$C_{30}$)alkyl ester of unsaturated carboxylic acid type corresponds to the monomer of formula (III) below:

in which $R_2$ denotes H or $CH_3$ or $C_2H_5$ (that is to say acrylate, methacrylate or ethacrylate units) and preferably H (acrylate units) or $CH_3$ (methacrylate units), $R_3$ denoting a $C_{10}$-$C_{30}$ and preferably $C_{12}$-$C_{22}$ alkyl radical.

($C_{10}$-$C_{30}$) alkyl esters of unsaturated carboxylic acids according to the invention include, for example, lauryl acrylate, stearyl acrylate, decyl acrylate, isodecyl acrylate and dodecyl acrylate, and the corresponding methacrylates, lauryl methacrylate, stearyl methacrylate, decyl methacrylate, isodecyl methacrylate and dodecyl methacrylate.

Anionic polymers of this type are described and prepared, for example, according to U.S. Pat. Nos. 3,915,921 and 4,509,949.

Among the anionic associative polymers of this type that will be used more particularly are polymers formed from a monomer mixture comprising:
(i) essentially acrylic acid,
(ii) an ester of formula (III) described above in which $R_2$ denotes H or $CH_3$, $R_3$ denoting an alkyl radical containing from 12 to 22 carbon atoms,
(iii) and a crosslinking agent, which is a well-known copolymerizable polyethylenic unsaturated monomer, for instance diallyl phthalate, allyl (meth)acrylate, divinylbenzene, (poly)ethylene glycol dimethacrylate and methylenebisacrylamide.

Among anionic associative polymers of this type that will be used more particularly are those consisting of from 95% to 60% by weight of acrylic acid (hydrophilic unit), 4% to 40% by weight of $C_{10}$-$C_{30}$ alkyl acrylate (hydrophobic unit) and 0% to 6% by weight of crosslinking polymerizable monomer, or alternatively those consisting of from 98% to 96% by weight of acrylic acid (hydrophilic unit), 1% to 4% by weight of $C_{10}$-$C_{30}$ alkyl acrylate (hydrophobic unit) and 0.1% to 0.6% by weight of crosslinking polymerizable monomer such as those described above.

Among said above polymers, those most particularly preferred according to the present invention are the products sold by the company Goodrich under the trade names Pemulen TR1, Pemulen TR2 and Carbopol 1382, and even more preferentially Pemulen TR1, and the product sold by the company SEPPIC under the name Coatex SX.

(III) maleic anhydride/$C_{30}$-$C_{38}$ α-olefin/alkyl maleate terpolymers, such as the product (maleic anhydride/$C_{30}$-$C_{38}$ α-olefin/isopropyl maleate copolymer) sold under the name Performa V 1608 by the company Newphase Technologies.

(IV) acrylic terpolymers comprising:
(a) about 20% to 70% by weight of a carboxylic acid containing (α,β-monoethylenic unsaturation,
(b) about 20% to 80% by weight of a non-surfactant monomer containing α,β-monoethylenic unsaturation other than (a),
(c) about 0.5% to 60% by weight of a nonionic monourethane which is the product of reaction of a monohydric surfactant with a monoisocyanate containing monoethylenic unsaturation, such as those described in patent application EP-A-0 173 109 and more particularly the terpolymer described in Example 3, namely a methacrylic acid/methyl acrylate/biphenyl dimethyl-meta-isopropenylbenzylisocyanate ethoxylated (40 EO) terpolymer, as an aqueous 25% dispersion.

(V) copolymers comprising among their monomers a carboxylic acid containing α,β-monoethylenic unsaturation and an ester of a carboxylic acid containing α,β-monoethylenic unsaturation and of an oxyalkylenated fatty alcohol.

Preferentially, these compounds also comprise as monomer an ester of a carboxylic acid containing α,β-monoethylenic unsaturation and of a $C_1$-$C_4$ alcohol.

An example of a compound of this type which may be mentioned is Aculyn 22 sold by the company Rohm & Haas, which is a methacrylic acid/ethyl acrylate/stearyl methacrylate oxyalkylenated terpolymer.

Associative Polymers of Cationic Type

Among these, mention may be made of:

(I) the cationic associative polyurethanes whose family has been described by the Applicant in French patent application No. 0 009 609; they may be represented by the general formula (Ia) below:

$$R—X—(P)_n-[L-(Y)_m]_r-L'-(P')_p—X'—R' \tag{Ia}$$

in which:
R and R', which may be identical or different, represent a hydrophobic group or a hydrogen atom;
X and X', which may be identical or different, represent a group comprising an amine function optionally bearing a hydrophobic group, or alternatively a group L";
L, L' and L", which may be identical or different, represent a group derived from a diisocyanate;
P and P', which may be identical or different, represent a group comprising an amine function optionally bearing a hydrophobic group;
Y represents a hydrophilic group;
r is an integer between 1 and 100, preferably between 1 and 50 and in particular between 1 and 25,
n, m and p each range, independently of each other, from 0 to 1000;
the molecule containing at least one protonated or quaternized amine function and at least one hydrophobic group.

In one preferred embodiment of these polyurethanes, the only hydrophobic groups are the groups R and R' at the chain ends.

One preferred family of cationic associative polyurethanes is the one corresponding to formula (Ia) described above and in which:
R and R' both independently represent a hydrophobic group,
X and X' each represent a group L",
n and p are between 1 and 1000, and
L, L', L", P, P', Y and m have the meaning given above.

Another preferred family of cationic associative polyurethanes is the one corresponding to formula (Ia) above in which:
R and R' both independently represent a hydrophobic group, X and X' each represent a group L", n and p are 0, and L, L', L", Y and m have the meaning given above.

The fact that n and p are 0 means that these polymers do not comprise units derived from a monomer containing an amine function, incorporated into the polymer during the polycondensation. The protonated amine functions of these polyurethanes result from the hydrolysis of excess isocyanate functions, at the chain end, followed by alkylation of the primary amine functions formed with alkylating agents containing a hydrophobic group, i.e. compounds of the type RQ or R'Q, in which R and R' are as defined above and Q denotes a leaving group such as a halide, a sulfate, etc.

Yet another preferred family of cationic associative polyurethanes is the one corresponding to formula (Ia) above in which:
R and R' both independently represent a hydrophobic group, X and X' both independently represent a group comprising a quaternary amine,
n and p are 0, and
L, L', Y and m have the meaning given above.

The number-average molecular mass of the cationic associative polyurethanes is preferably between 400 and 500 000, in particular between 1000 and 400 000 and ideally between 1000 and 300 000.

The expression "hydrophobic group" means a radical or polymer containing a saturated or unsaturated, linear or branched hydrocarbon-based chain, which may contain one or more hetero atoms such as P, O, N or S, or a radical containing a perfluoro or silicone chain. When the hydrophobic group denotes a hydrocarbon-based radical, it comprises at least 10 carbon atoms, preferably from 10 to 30 carbon atoms, in particular from 12 to 30 carbon atoms and more preferably from 18 to 30 carbon atoms.

Preferentially, the hydrocarbon-based group is derived from a monofunctional compound.

By way of example, the hydrophobic group may be derived from a fatty alcohol such as stearyl alcohol, dodecyl alcohol or decyl alcohol. It may also denote a hydrocarbon-based polymer such as, for example, polybutadiene.

When X and/or X' denote(s) a group comprising a tertiary or quaternary amine, X and/or X' may represent one of the following formulae:

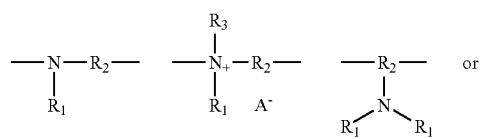

for X

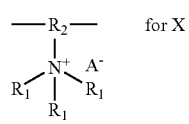

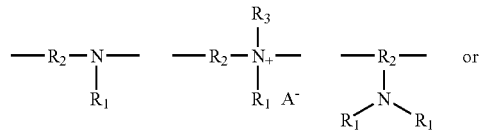

for X'

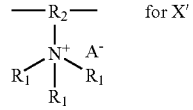

in which:
$R_2$ represents a linear or branched alkylene radical containing from 1 to 20 carbon atoms, optionally comprising a saturated or unsaturated ring, or an arylene radical, one or more of the carbon atoms possibly being replaced with a hetero atom chosen from N, S, O and P;
$R_1$ and $R_3$, which may be identical or different, denote a linear or branched $C_1$-$C_{30}$ alkyl or alkenyl radical or an aryl radical, at least one of the carbon atoms possibly being replaced with a hetero atom chosen from N, S, O and P;

A⁻ is a physiologically acceptable counter-ion.

The groups L, L' and L" represent a group of formula:

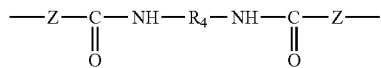

in which:

Z represents —O—, —S— or —NH—; and $R_4$ represents a linear or branched alkylene radical containing from 1 to 20 carbon atoms, optionally comprising a saturated or unsaturated ring or an arylene radical, one or more of the carbon atoms possibly being replaced with a hetero atom chosen from N, S, O and P.

The groups P and P' comprising an amine function may represent at least one of the following formulae:

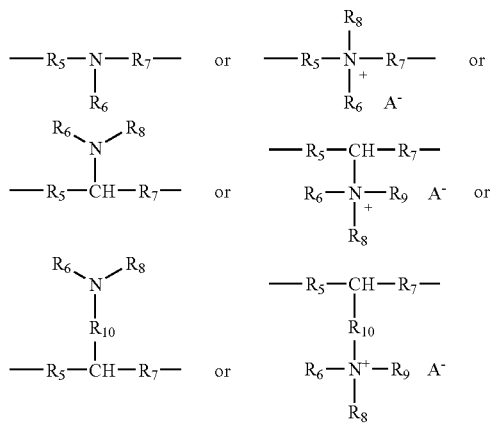

in which:

$R_5$ and $R_7$ have the same meanings as $R_2$ defined above;

$R_6$, $R_8$ and $R_9$ have the same meanings as $R_1$ and $R_3$ defined above;

$R_{10}$ represents a linear or branched, optionally unsaturated alkylene group which may contain one or more hetero atoms chosen from N, O, S and P, and A⁻ is a physiologically acceptable counter-ion.

As regards the meaning of Y, the term "hydrophilic group" means a polymeric or non-polymeric water-soluble group.

By way of example, when it is not a polymer, mention may be made of ethylene glycol, diethylene glycol and propylene glycol.

When it is a hydrophilic polymer, in accordance with one preferred embodiment, mention may be made, for example, of polyethers, sulfonated polyesters, sulfonated polyamides or a mixture of these polymers. The hydrophilic compound is preferentially a polyether and in particular a poly(ethylene oxide) or poly(propylene oxide).

The cationic associative polyurethanes of formula (Ia) according to the invention are formed from diisocyanates and from various compounds with functions containing labile hydrogen. The functions containing labile hydrogen may be alcohol, primary or secondary amine or thiol functions giving, after reaction with the diisocyanate functions, polyurethanes, polyureas and polythioureas, respectively. The term "polyurethanes" in the present invention encompasses these three types of polymer, namely polyurethanes per se, polyureas and polythioureas, and also copolymers thereof.

A first type of compound involved in the preparation of the polyurethane of formula (Ia) is a compound comprising at least one unit containing an amine function. This compound may be multifunctional, but the compound is preferentially difunctional, that is to say that, according to one preferential embodiment, this compound comprises two labile hydrogen atoms borne, for example, by a hydroxyl, primary amine, secondary amine or thiol function. A mixture of multifunctional and difunctional compounds in which the percentage of multifunctional compounds is low may also be used.

As mentioned above, this compound may comprise more than one unit containing an amine function. In this case, it is a polymer bearing a repetition of the unit containing an amine function.

Compounds of this type may be represented by one of the following formulae:

$HZ\text{-}(P)_n\text{-}ZH$

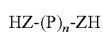

or $HZ\text{-}(P')_p\text{-}ZH$

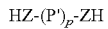

in which Z, P, P', n and p are as defined above.

Examples of compounds containing an amine function that may be mentioned include N-methyldiethanolamine, N-tert-butyldiethanolamine and N-sulfoethyldiethanolamine.

The second compound involved in the preparation of the polyurethane of formula (Ia) is a diisocyanate corresponding to the formula:

$O=C=N-R_4-N=C=O$

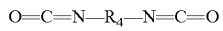

in which $R_4$ is as defined above.

By way of example, mention may be made of methylenediphenyl diisocyanate, methylenecyclohexane diisocyanate, isophorone diisocyanate, toluene diisocyanate, naphthalene diisocyanate, butane diisocyanate and hexane diisocyanate.

A third compound involved in the preparation of the polyurethane of formula (Ia) is a hydrophobic compound intended to form the terminal hydrophobic groups of the polymer of formula (Ia).

This compound consists of a hydrophobic group and of a function containing a labile hydrogen, for example a hydroxyl, primary or secondary amine, or thiol function.

By way of example, this compound may be a fatty alcohol such as, in particular, stearyl alcohol, dodecyl alcohol or decyl alcohol. When this compound comprises a polymeric chain, it may be, for example, [lacuna]-hydroxylated hydrogenated polybutadiene.

The hydrophobic group of the polyurethane of formula (Ia) may also result from the quaternization reaction of the tertiary amine of the compound comprising at least one tertiary amine unit. Thus, the hydrophobic group is introduced via the quaternizing agent. This quaternizing agent is a compound of the type RQ or R'Q, in which R and R' are as defined above and Q denotes a leaving group such as a halide, a sulfate, etc.

The cationic associative polyurethane may also comprise a hydrophilic block. This block is provided by a fourth type of compound involved in the preparation of the polymer. This compound may be multifunctional. It is preferably difunctional. It is also possible to have a mixture in which the percentage of multifunctional compound is low.

The functions containing a labile hydrogen are alcohol, primary or secondary amine or thiol functions. This compound may be a polymer terminated at the chain ends with one of these functions containing a labile hydrogen.

By way of example, when it is not a polymer, mention may be made of ethylene glycol, diethylene glycol and propylene glycol.

When it is a hydrophilic polymer, mention may be made, for example, of polyethers, sulfonated polyesters and sulfonated polyamides, or a mixture of these polymers. The hydrophilic compound is preferentially a polyether and especially a poly(ethylene oxide) or poly(propylene oxide).

The hydrophilic group termed Y in formula (Ia) is optional. Specifically, the units containing a quaternary amine or protonated function may suffice to provide the solubility or water-dispersibility required for this type of polymer in an aqueous solution. Although the presence of a hydrophilic group Y is optional, cationic associative polyurethanes comprising such a group are, however, preferred.

(II) quaternized cellulose derivatives and polyacrylates containing non-cyclic amino side groups.

The quaternized cellulose derivatives are in particular:

quaternized celluloses modified with groups comprising at least one fatty chain, such as alkyl, arylalkyl or alkylaryl groups comprising at least 8 carbon atoms, or mixtures thereof;

quaternized hydroxyethylcelluloses modified with groups comprising at least one fatty chain, such as alkyl, arylalkyl or alkylaryl groups comprising at least 8 carbon atoms, or mixtures thereof.

The alkyl radicals borne by the above quaternized celluloses or hydroxyethylcelluloses preferably comprise from 8 to 30 carbon atoms. The aryl radicals preferably denote phenyl, benzyl, naphthyl or anthryl groups.

Examples of quaternized alkylhydroxyethylcelluloses containing $C_8$-$C_{30}$ fatty chains that may be mentioned include the products Quatrisoft LM 200®, Quatrisoft LM-X 529-18-A®, Quatrisoft LM-X 529-18B® ($C_{12}$ alkyl) and Quatrisoft LM-X 529-8® ($C_{18}$ alkyl) sold by the company Amerchol and the products Crodacel QM®, Crodacel QL® ($C_{12}$ alkyl) and Crodacel QS® ($C_{18}$ alkyl) sold by the company Croda.

Amphoteric Associative Polymers

These are preferably chosen from polymers comprising at least one non-cyclic cationic unit. Even more particularly, the ones that are preferred are those prepared from or comprising 1 to 20 mol % of monomer comprising a fatty chain, preferably 1.5 to 15 mol % and even more particularly 1.5 to 6 mol %, relative to the total number of moles of monomers.

The amphoteric associative polymers that are preferred according to the invention comprise, or are prepared by copolymerizing:

1) at least one monomer of formula (Ia) or (Ib):

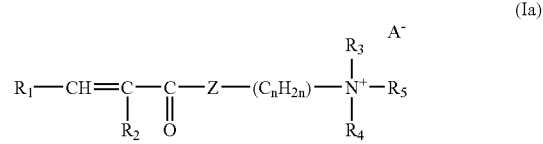

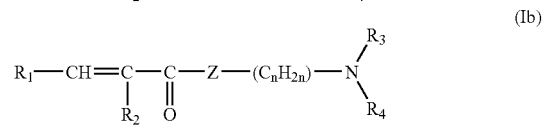

in which $R_1$ and $R_2$, which may be identical or different, represent a hydrogen atom or a methyl radical, $R_3$, $R_4$ and $R_5$, which may be identical or different, represent a linear or branched alkyl radical containing from 1 to 30 carbon atoms, Z represents an NH group or an oxygen atom, n is an integer from 2 to 5, $A^-$ is an anion derived from an organic or mineral acid, such as a methosulfate anion or a halide such as chloride or bromide;

2) at least one monomer of formula (II)

in which $R_6$ and $R_7$, which may be identical or different, represent a hydrogen atom or a methyl radical;

and 3) at least one monomer of formula (III):

in which $R_6$ and $R_7$, which may be identical or different, represent a hydrogen atom or a methyl radical, X denotes an oxygen or nitrogen atom and $R_8$ denotes a linear or branched alkyl radical containing from 1 to 30 carbon atoms;

at least one of the monomers of formula (Ia), (Ib) or (III) comprising at least one fatty chain.

The monomers of formulae (Ia) and (Ib) of the present invention are preferably chosen from the group consisting of:

dimethylaminoethyl methacrylate, dimethylaminoethyl acrylate, diethylaminoethyl methacrylate, diethylaminoethyl acrylate, dimethylaminopropyl methacrylate, dimethylaminopropyl acrylate, dimethylaminopropylmethacrylamide, dimethylaminopropylacrylamide, these monomers optionally being quaternized, for example with a $C_1$-$C_4$ alkyl halide or a $C_1$-$C_4$ dialkyl sulfate.

More particularly, the monomer of formula (Ia) is chosen from acrylamidopropyltrimethylammonium chloride and methacrylamidopropyltrimethyl ammonium chloride.

The monomers of formula (II) of the present invention are preferably chosen from the group consisting of acrylic acid, methacrylic acid, crotonic acid and 2-methylcrotonic acid. More particularly, the monomer of formula (II) is acrylic acid.

The monomers of formula (III) of the present invention are preferably chosen from the group consisting of $C_{12}$-$C_{22}$ and more particularly $C_{16}$-$C_{18}$ alkyl acrylates or methacrylates.

The monomers constituting the fatty-chain amphoteric polymers of the invention are preferably already neutralized and/or quaternized.

The ratio of the number of cationic charges/anionic charges is preferably equal to about 1.

The amphoteric associative polymers according to the invention preferably comprise from 1 mol % to 10 mol % of the monomer comprising a fatty chain (monomer of formula (Ia), (Ib) or (III)), and preferably from 1.5 mol % to 6 mol %.

The weight-average molecular weights of the amphoteric associative polymers according to the invention may range from 500 to 50 000 000 and are preferably between 10 000 and 5 000 000.

The amphoteric associative polymers according to the invention may also contain other monomers such as nonionic monomers and in particular such as $C_1$-$C_4$ alkyl acrylates or methacrylates.

Amphoteric associative polymers according to the invention are described and prepared, for example, in patent application WO 98/44012.

Among the amphoteric associative polymers according to the invention, the ones that are preferred are acrylic acid/(meth)acrylamidopropyltrimethylammonium chloride/stearyl methacrylate terpolymers.

In the dye composition according to the invention, an associative polymer of nonionic type is preferably used.

Associative Polymers of Nonionic Type

According to the invention, these are preferably chosen from:

(1) celluloses modified with groups comprising at least one fatty chain;

examples that may be mentioned include:
hydroxyethylcelluloses modified with groups comprising at least one fatty chain, such as alkyl, arylalkyl or alkylaryl groups, or mixtures thereof, and in which the alkyl groups are preferably $C_8$-$C_{22}$, for instance the product Natrosol Plus Grade 330 CS® ($C_{16}$ alkyls) sold by the company Aqualon, or the product Bermocoll EHM 100® sold by the company Berol Nobel,
those modified with alkylphenyl polyalkylene glycol ether groups, such as the product Amercell Polymer HM-1500® (nonylphenyl polyethylene glycol (15) ether) sold by the company Amerchol.

(2) hydroxypropyl guars modified with groups comprising at least one fatty chain, such as the product Esaflor HM 22® ($C_{22}$ alkyl chain) sold by the company Lamberti, and the products RE210-18® ($C_{14}$ alkyl chain) and RE205-1® ($C_{20}$ alkyl chain) sold by the company Rhône-Poulenc.

(3) copolymers of vinylpyrrolidone and of fatty-chain hydrophobic monomers; examples that may be mentioned include:
the products Antaron V216® or Ganex V216® (vinylpyrrolidone/hexadecene copolymer) sold by the company I.S.P.
the products Antaron V220® or Ganex V220® (vinylpyrrolidone/eicosene copolymer) sold by the company I.S.P.

(4) copolymers of $C_1$-$C_6$ alkyl methacrylates or acrylates and of amphiphilic monomers comprising at least one fatty chain, such as, for example, the oxyethylenated methyl acrylate/stearyl acrylate copolymer sold by the company Goldschmidt under the name Antil 208®.

(5) copolymers of hydrophilic methacrylates or acrylates and of hydrophobic monomers comprising at least one fatty chain, such as, for example, the polyethylene glycol methacrylate/lauryl methacrylate copolymer.

(6) polyurethane polyethers comprising in their chain both hydrophilic blocks usually of polyoxyethylenated nature and hydrophobic blocks which may be aliphatic sequences alone and/or cycloaliphatic and/or aromatic sequences.

(7) polymers with an aminoplast ether skeleton containing at least one fatty chain, such as the Pure Thix® compounds sold by the company Sud-Chemie.

Preferably, the polyurethane polyethers comprise at least two hydrocarbon-based lipophilic chains containing from 6 to 30 carbon atoms, separated by a hydrophilic block, the hydrocarbon-based chains possibly being pendent chains, or chains at the end of the hydrophilic block. In particular, it is possible for one or more pendent chains to be included. In addition, the polymer may comprise a hydrocarbon-based chain at one end or at both ends of a hydrophilic block.

The polyurethane polyethers may be multiblock, in particular in triblock form. Hydrophobic blocks may be at each end of the chain (for example: triblock copolymer with a hydrophilic central block) or distributed both at the ends and in the chain (for example: multiblock copolymer). These same polymers may also be graft polymers or starburst polymers.

The nonionic fatty-chain polyurethane polyethers may be triblock copolymers in which the hydrophilic block is a polyoxyethylenated chain comprising from 50 to 1000 oxyethylene groups. The nonionic polyurethane polyethers comprise a urethane linkage between the hydrophilic blocks, whence arises the name.

By extension, also included among the nonionic fatty-chain polyurethane polyethers are those in which the hydrophilic blocks are linked to the lipophilic blocks via other chemical bonds.

As examples of nonionic fatty-chain polyurethane polyethers that may be used in the invention, mention may also be made of Rheolate 205® containing a urea function, sold by the company Rheox, or the Rheolates® 208, 204 or 212, and also Acrysol RM 184®.

Mention may also be made of the product Elfacos T210® containing a $C_{12-14}$ alkyl chain, and the product Elfacos T212® containing a $C_{18}$ alkyl chain, from Akzo.

The product DW 1206B® from Rohm & Haas containing a $C_{20}$ alkyl chain and a urethane linkage, sold at a solids content of 20% in water, may also be used.

It is also possible to use solutions or dispersions of these polymers, especially in water or in aqueous-alcoholic medium. Examples of such polymers that may be mentioned are Rheolate® 255, Rheolate® 278 and Rheolate® 244 sold by the company Rheox. The products DW 1206F and DW 1206J sold by the company Rohm & Haas may also be used.

The polyurethane polyethers that may be used according to the invention are in particular those described in the article by G. Fonnum, J. Bakke and Fk. Hansen—Colloid Polym. Sci 271, 380.389 (1993).

Even more particularly, according to the invention, it is preferred to use a polyurethane polyether that may be obtained by polycondensation of at least three compounds comprising (i) at least one polyethylene glycol comprising from 150 to 180 mol of ethylene oxide, (ii) stearyl alcohol or decyl alcohol, and (iii) at least one diisocyanate.

Such polyurethane polyethers are sold especially by the company Rohm & Haas under the names Aculyn 46® and Aculyn 44® [Aculyn 46® is a polycondensate of polyethylene glycol containing 150 or 180 mol of ethylene oxide, of stearyl alcohol and of methylenebis(4-cyclohexyl isocyanate) (SMDI), at 15% by weight in a matrix of maltodextrin (4%) and water (81%); Aculyn 44® is a polycondensate of polyethylene glycol containing 150 or 180 mol of ethylene oxide, of decyl alcohol and of methylenebis(4-cyclohexyl isocyanate) (SMDI), at 35% by weight in a mixture of propylene glycol (39%) and water (26%)].

The associative polymers of nonionic, anionic, cationic or amphoteric type are preferably used in an amount that can range from about 0.1% to 10% by weight relative to the total weight of the dye composition. More preferably, this amount ranges from about 0.5% to 5% by weight and even more particularly from about 1% to 3% by weight.

Oxidation Dyes

The oxidation dyes that may be used according to the invention are chosen from oxidation bases and/or couplers.

The compositions according to the invention preferably contain at least one oxidation base.

The nature of these oxidation bases is not critical. They may be chosen especially from ortho- and para-phenylenediamines, double bases, ortho- and para-aminophenols, the heterocyclic bases below, and also the addition salts thereof with an acid.

Mention may be made especially of:

(I) the para-phenylenediamines of formula (I) below, and the addition salts thereof with an acid:

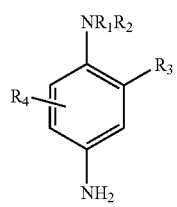

(I)

in which:

$R_1$ represents a hydrogen atom, a $C_1$-$C_4$ alkyl radical, a $C_1$-$C_4$ monohydroxyalkyl radical, a $C_2$-$C_4$ polyhydroxyalkyl radical, a ($C_1$-$C_4$)alkoxy($C_1$-$C_4$)alkyl radical or a $C_1$-$C_4$ alkyl radical substituted with a nitrogenous, phenyl or 4'-aminophenyl group;

$R_2$ represents a hydrogen atom, a $C_1$-$C_4$ alkyl radical, a $C_1$-$C_4$ monohydroxyalkyl radical, a $C_2$-$C_4$ polyhydroxyalkyl radical, a ($C_1$-$C_4$)alkoxy(Cl-$C_4$)alkyl radical or a $C_1$-$C_4$ alkyl radical substituted with a nitrogenous group;

$R_1$ and $R_2$ may also form, with the nitrogen atom that bears them, a 5- or 6-membered nitrogen heterocycle optionally substituted with one or more alkyl, hydroxyl or ureido groups;

$R_3$ represents a hydrogen atom, a halogen atom such as a chlorine atom, a $C_1$-$C_4$ alkyl radical, a sulfo radical, a carboxyl radical, a $C_1$-$C_4$ monohydroxyalkyl radical, a $C_1$-$C_4$ hydroxyalkoxy radical, an acetylamino($C_1$-$C_4$) alkoxy radical, a mesylamino($C_1$-$C_4$)-alkoxy radical or a carbamoylamino($C_1$-$C_4$)alkoxy radical, $R_4$ represents a hydrogen or halogen atom or a $C_1$-$C_4$ alkyl radical.

Among the nitrogenous groups of formula (I) above, mention may be made especially of amino, mono($C_1$-$C_4$) alkylamino, di($C_1$-$C_4$)alkylamino, tri($C_1$-$C_4$)alkylamino, monohydroxy($C_1$-$C_4$)alkylamino, imidazolinium and ammonium radicals.

Among the para-phenylenediamines of formula (I) above, mention may be made more particularly of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-N,N-bis(β-hydroxyethyl)-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine and 2-β-hydroxyethyloxy-para-phenylenediamine, 2-β-acetylaminoethyloxy-para-phenylenediamine, N-(β-methoxyethyl)-para-phenylenediamine and 2-methyl-1-N-β-hydroxyethyl-para-phenylenediamine, and the addition salts thereof with an acid.

Among the para-phenylenediamines of formula (I) above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine and 2-chloro-para-phenylenediamine, and the addition salts thereof with an acid, are most particularly preferred.

(II) According to the invention, the term double bases means compounds containing at least two aromatic nuclei bearing amino and/or hydroxyl groups.

Among the double bases that can be used as oxidation bases in the dye compositions in accordance with the invention, mention may be made especially of the compounds corresponding to formula (II) below, and the addition salts thereof with an acid:

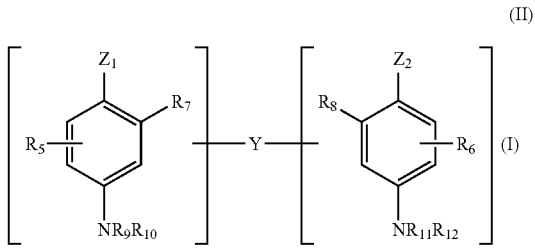

(II)

in which:

$Z_1$ and $Z_2$, which may be identical or different, represent a hydroxyl or —$NH_2$ radical which may be substituted with a $C_1$-$C_4$ alkyl radical or with a linker arm Y;

the linker arm Y represents a linear or branched alkylene chain containing from 1 to 14 carbon atoms, which may be interrupted by or terminated with one or more nitrogenous groups and/or one or more hetero atoms such as oxygen, sulfur or nitrogen atoms, and optionally substituted with one or more hydroxyl or $C_1$-$C_6$ alkoxy radicals;

$R_5$ and $R_6$ represent a hydrogen or halogen atom, a $C_1$-$C_4$ alkyl radical, a $C_1$-$C_4$ monohydroxyalkyl radical, a $C_2$-$C_4$ polyhydroxyalkyl radical, a $C_1$-$C_4$ aminoalkyl radical or a linker arm Y;

$R_7$, $R_8$, $R_9$, $R_{10}$, $R_{11}$ and $R_{12}$, which may be identical or different, represent a hydrogen atom, a linker arm Y or a $C_1$-$C_4$ alkyl radical;

it being understood that the compounds of formula (II) contain only one linker arm Y per molecule.

Among the nitrogenous groups of formula (II) above, mention may especially be made of amino, mono($C_1$-$C_4$) alkylamino, di($C_1$-$C_4$)alkylamino, tri($C_1$-$C_4$)alkylamino, monohydroxy($C_1$-$C_4$)alkylamino, imidazolinium and ammonium radicals.

Among the double bases of formula (II) above, mention may be made more particularly of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(3-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,5-dioxaoctane, and the addition salts thereof with an acid.

Among these double bases of formula (II), N,N'-bis(β-hydroxyethyl)-N,N'-bis(4'-aminophenyl)-1,3-diaminopropanol and 1,8-bis(2,5-diaminophenoxy)-3,5-dioxaoctane, or one of the addition salts thereof with an acid, are particularly preferred.

(III) The para-aminophenols corresponding to formula (III) below, and the addition salts thereof with an acid:

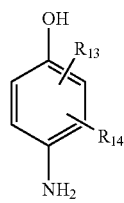

(III)

in which:

$R_{13}$ represents a hydrogen atom, a halogen atom such as fluorine, or a $C_1$-$C_4$ alkyl, $C_1$-$C_4$ monohydroxyalkyl, ($C_1$-$C_4$)alkoxy($C_1$-$C_4$)alkyl, $C_1$-$C_4$ aminoalkyl or hydroxy ($C_1$-$C_4$)alkylamino($C_1$-$C_4$)alkyl radical, $R_{14}$ represents a hydrogen atom, a halogen atom such as fluorine, or a $C_1$-$C_4$-alkyl, $C_1$-$C_4$ monohydroxyalkyl, $C_2$-$C_4$ polyhydroxyalkyl, $C_1$-$C_4$ aminoalkyl, $C_1$-$C_4$ cyanoalkyl or ($C_1$-$C_4$)alkoxy-($C_1$-$C_4$)alkyl radical.

Among the para-aminophenols of formula (III) above, mention may be made more particularly of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(β-hydroxyethylaminomethyl)phenol, and the addition salts thereof with an acid.

(IV) The ortho-aminophenols that can be used as oxidation bases in the context of the present invention are chosen especially from 2-aminophenol, 2-amino-1-hydroxy-5-methylbenzene, 2-amino-1-hydroxy-6-methylbenzene and 5-acetamido-2-aminophenol, and the addition salts thereof with an acid.

(V) Among the heterocyclic bases that can be used as oxidation bases in the dye compositions in accordance with the invention, mention may be made more particularly of pyridine derivatives, pyrimidine derivatives and pyrazole derivatives, and the addition salts thereof with an acid.

Among the pyridine derivatives, mention may be made more particularly of the compounds described, for example, in patents GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid.

Among the pyrimidine derivatives, mention may be made more particularly of the compounds described, for example, in German patent DE 2 359 399 or Japanese patents JP 88-169 571 and JP 91-10659 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in patent application FR-A-2 750 048 and among which mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]-pyrimidin-7-ol; 3-aminopyrazolo[1,5-a]pyrimidin-5-ol; 2-(3-aminopyrazolo[1,5-a]pyrimidin-7-ylamino)ethanol; 2-(7-aminopyrazolo[1,5-a]pyrimidin-3-ylamino)ethanol; 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol; 5,6-dimethylpyrazolo[1,5-a]pyrimidine-3,7-diamine; 2,6-dimethylpyrazolo[1,5-a]pyrimidine-3,7-diamine; 2,5,N7,N7-tetramethylpyrazolo[1,5-a]pyrimidine-3,7-diamine and 3-amino-5-methyl-7-imidazolylpropylamino-pyrazolo[1,5-a]pyrimidine and the addition salts thereof and the tautomeric forms thereof, when a tautomeric equilibrium exists, and the addition salts thereof with an acid.

Among the pyrazole derivatives, mention may be made more particularly of the compounds described in patents DE 3 843 892, DE 4 133 957 and patent applications WO 94/08969, WO 94/08970, FR-A-2 733 749 and DE 195 43 988, such as 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-(☐-hydroxyethyl)pyrazole, 4,5-diamino-1-ethyl-3-methylpyrazole, 4,5-diamino-1-ethyl-3-(4'-methoxyphenyl) pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)

amino-1,3-dimethyl-pyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl) amino-1-methylpyrazole, and the addition salts thereof with an acid.

According to the present invention, the oxidation bases preferably represent from 0.0005% to 12% by weight approximately relative to the total weight of the composition and even more preferably from 0.005% to 8% by weight approximately relative to this weight.

The dye composition in accordance with the invention may contain one or more couplers chosen from those conventionally used in oxidation dyeing and especially from meta-aminophenols, meta-phenylenediamines and meta-diphenols, naphthols and heterocyclic couplers such as, for example, indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles and quinolines, and the addition salts thereof with an acid.

These couplers are chosen more particularly from 2,4-diamino-1-(□-hydroxyethyloxy)benzene, 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-β-hydroxyethylindole, 6-hydroxyindoline, 2,6-dihydroxy-4-methylpyridine, 1H-3-methylpyrazol-5-one, 1-phenyl-3-methylpyrazol-5-one, 2-amino-3-hydroxypyridine, 3,6-dimethylpyrazolo[3,2-c]-1,2,4-triazole and 2,6-dimethylpyrazolo[1,5-b]-1,2,4-triazole, and the addition salts thereof with an acid.

In general, the coupler(s) preferably represent from 0.0001% to 15% by weight approximately relative to the total weight of the dye composition and even more preferably from 0.001% to 10% by weight approximately.

The addition salts with an acid of these oxidation dyes (bases and/or couplers) are chosen especially from the hydrochlorides, hydrobromides, sulfates, tartrates, lactates and acetates.

The dye composition in accordance with the invention comprising at least one oxidation dye may also contain one or more direct dyes, especially to modify the shades obtained with the bases and/or couplers, by enriching them with glints. These direct dyes may especially be chosen from neutral, cationic or anionic nitro dyes, azo dyes or anthraquinone dyes, conventionally used or those described especially in patent applications FR-2 782 450, 2 782 451, 2 782 452 and EP-1 025 834, in a weight proportion from about 0.001% to 20% and preferably from 0.01% to 10% of the total weight of the composition.

Direct Dyes

The direct dyes that are suitable for direct dyeing are those described above and those that are more particularly suitable for lightening dyeing (i.e. dyeing with an oxidizing agent) are those described especially in patent applications FR-2 782 450, 2 782 451, 2 782 452 and EP-1 025 834.

Medium

The medium for the composition that is suitable for dyeing is preferably an aqueous medium consisting of water that may advantageously comprise cosmetically acceptable organic solvents including, more particularly, alcohols such as ethyl alcohol, isopropyl alcohol, benzyl alcohol and phenylethyl alcohol, or glycols or glycol ethers such as, for example, the monomethyl, monoethyl or monobutyl ethers of ethylene glycol, propylene glycol or ethers thereof, for instance propylene glycol monomethyl ether, butylene glycol, dipropylene glycol, and also diethylene glycol alkyl ethers, for instance diethylene glycol monoethyl ether or monobutyl ether. The solvents may then be present in concentrations of between about 0.5% and 20% and preferably between about 2% and 10% by weight relative to the total weight of the composition.

The dye composition and/or the oxidizing composition (in the case of oxidation dyeing or lightening dyeing) may more particularly also comprise at least one anionic, nonionic, cationic, amphoteric or zwitterionic surfactant, in a proportion of at least 0.01% by weight relative to the total weight of the composition, and preferably a surfactant of nonionic nature.

These surfactants may be chosen from:

Nonionic Surfactants:

The nonionic surfactants are, themselves also, compounds that are well known per se (see in particular in this respect "Handbook of Surfactants" by M. R. Porter, published by Blackie & Son (Glasgow and London), 1991, pp. 116-178), and their nature is not critical in the context of the present invention. Thus, they can be chosen in particular from (nonlimiting list) polyethoxylated, polypropoxylated, alkylphenols, alpha-diols or alcohols having a fatty chain containing, for example, 8 to 18 carbon atoms, it being possible for the number of ethylene oxide or propylene oxide groups to range in particular from 2 to 50. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide, polyglycerolated fatty amides containing on average 1 to 5, and in particular 1.5 to 4, glycerol groups; polyethoxylated fatty amines preferably having 2 to 30 mol of ethylene oxide; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, and amine oxides such as ($C_{10}$-$C_{14}$) alkylamine oxides or N-acylaminopropylmorpholine oxides.

Anionic Surfactants:

By way of example of anionic surfactants which can be used, alone or as mixtures, in the context of the present invention, mention may be made in particular (nonlimiting list) of salts (in particular alkali metal salts, especially sodium salts, ammonium salts, amine salts, amino alcohol salts or magnesium salts) of the following compounds: alkyl sulfates, alkyl ether sulfates, alkylamido ether sulfates, alkylarylpolyether sulfates, monoglyceride sulfates; alkyl sulfonates, alkyl phosphates, alkylamide sulfonates, alkylaryl sulfonates, α-olefin sulfonates, paraffin sulfonates; ($C_6$-$C_{24}$) alkyl sulfosuccinates, ($C_6$-$C_{24}$)alkyl ether sulfosuccinates, ($C_6$-$C_{24}$)alkylamide sulfosuccinates; ($C_6$-$C_{24}$)alkyl sulfoacetates; ($C_6$-$C_{24}$)acyl sarcosinates; and ($C_6$-$C_{24}$)acyl glutamates. It is also possible to use ($C_6$-$C_{24}$)alkylpolyglycoside carboxylic esters such as alkylglucoside citrates, alkylpolyglycoside tartrates and alkylpolyglycoside sulfosuccinates, alkylsulfosuccinamates; acyl isethionates and N-acyl taurates, the alkyl or acyl radical of all of these different compounds preferably containing from 12 to 20 carbon atoms and the aryl radical preferably denoting a phenyl or benzyl group. Among the anionic surfactants which can also be used, mention may also be made of fatty acid salts such as oleic, ricinoleic, palmitic and stearic acid salts, coconut oil acid or hydrogenated coconut oil acid; acyl lactylates in which the acyl radical contains 8 to 20 carbon atoms. It is also possible to use alkyl D-galactoside uronic acids and their salts, polyoxyalkylenated ($C_6$-$C_{24}$)alkyl ether carboxylic acids, polyoxyalkylenated ($C_6$-$C_{24}$)alkylaryl ether carboxylic acids, polyoxyalkylenated ($C_6$-$C_{24}$)alkylamido ether carboxylic acids and their salts, in particular those containing from 2 to 50 alkylene oxide groups in particular ethylene oxide groups, and mixtures thereof.

Amphoteric or Zwitterionic Surfactants:

The amphoteric or zwitterionic surfactants, whose nature is not critical in the context of the present invention, can be, in particular (nonlimiting list), aliphatic secondary or tertiary amine derivatives in which the aliphatic radical is a linear or branched chain containing 8 to 18 carbon atoms and containing at least one water-solubilizing anionic group (for example carboxylate, sulfonate, sulfate, phosphate or phosphonate); mention may also be made of ($C_8$-$C_{20}$)alkylbetaines, sulfobetaines, ($C_8$-$C_{20}$)alkylamido($C_1$-$C_6$)alkylbetaines or ($C_8$-$C_{20}$)alkylamido($C_1$-$C_6$)alkylsulfobetaines.

Among the amine derivatives, mention may be made of the products sold under the name Miranol, as described in U.S. Pat. Nos. 2,528,378 and 2,781,354 and classified in the CTFA dictionary, 3rd edition, 1982, under the names Amphocarboxyglycinates and Amphocarboxypropionates, with the respective structures:

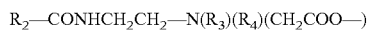

in which: $R_2$ denotes an alkyl radical of an acid $R_2$—COOH present in hydrolyzed coconut oil, a heptyl, nonyl or undecyl radical, $R_3$ denotes a beta-hydroxyethyl group and $R_4$ denotes a carboxymethyl group;

and

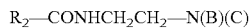

in which:

B represents —$CH_2CH_2OX'$, C represents —$(CH_2)_z$—Y', with z=1 or 2,

X' denotes the —$CH_2CH_2$—COOH group or a hydrogen atom,

Y' denotes —COOH or the —$CH_2$—CHOH—$SO_3H$ radical, $R_2'$ denotes an alkyl radical of an acid $R_9$—COOH present in coconut oil or in hydrolyzed linseed oil, an alkyl radical, in particular a $C_7$, $C_9$, $C_{11}$ or $C_{13}$ alkyl radical, a $C_{17}$ alkyl radical and its iso form, or an unsaturated $C_{17}$ radical.

These compounds are classified in the CTFA dictionary, 5th edition, 1993, under the names Disodium Cocoamphodiacetate, Disodium Lauroamphodiacetate, Disodium Caprylamphodiacetate, Disodium Caryloamphodiacetate, Disodium Cocoamphodipropionate, Disodium Lauroamphopropionate, Disodium Caprylamphodipropionate, Disodium Caryloamphodipropionate, Lauroamphodipropionic acid and Cocoamphodipropionic acid.

By way of example, mention may be made of the cocoamphodiacetate sold under the trade name Miranol® C2M concentrate by the company Rhodia Chimie.

Cationic Surfactants:

Among the cationic surfactants, mention may be made in particular (nonlimiting list) of: salts of optionally polyoxyalkylenated primary, secondary or tertiary fatty amines; quaternary ammonium salts such as tetraalkylammonium, alkylamidoalkyltrialkylammonium, trialkylbenzylammonium, trialkylhydroxyalkylammonium or alkylpyridinium chlorides or bromides; imidazoline derivatives; or amine oxides of cationic nature.

The amounts of surfactants present in the dye composition according to the invention may range from 0.01% to 40% and preferably from 0.5% to 30% of the total weight of the composition.

Preferably, according to the invention, the dye composition and/or the oxidizing composition may more particularly also comprise at least one cationic or amphoteric polymer (other than the associative polymers and the polymers containing (i) acrylamide, (ii) dialkyldiallylammonium halide and (iii) acrylic acid units, according to the invention) in a proportion of at least 0.01% by weight relative to the total weight of the composition.

More particularly, according to the invention, said cationic or amphoteric polymers are in the dyeing part.

Cationic Polymers

For the purposes of the present invention, the term "cationic polymer" denotes any polymer containing cationic groups and/or groups that may be ionized into cationic groups.

The cationic polymers that may be used in accordance with the present invention may be chosen from all those already known per se as improving the cosmetic properties of the hair, i.e. especially those described in patent application EP-A-337 354 and in French patents FR-2 270 846, 2 383 660, 2 598 611, 2 470 596 and 2 519 863.

The cationic polymers that are preferred are chosen from those containing units comprising primary, secondary, tertiary and/or quaternary amine groups, which may either form part of the main polymer chain or may be borne by a side substituent directly attached thereto.

The cationic polymers used generally have a number-average molecular mass of between 500 and $5\times10^6$ approximately and preferably between $10^3$ and $3\times10^6$ approximately.

Among the cationic polymers that may be mentioned more particularly are polymers of the polyamine, polyamino amide and polyquaternary ammonium type.

These are known products. They are described in particular in French patents Nos 2 505 348 and 2 542 997. Among said polymers, mention may be made of:

(1) homopolymers or copolymers derived from acrylic or methacrylic esters or amides and comprising at least one of the units of formula (I), (II), (III) or (IV) below:

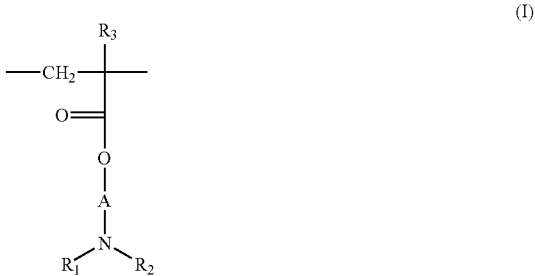

-continued

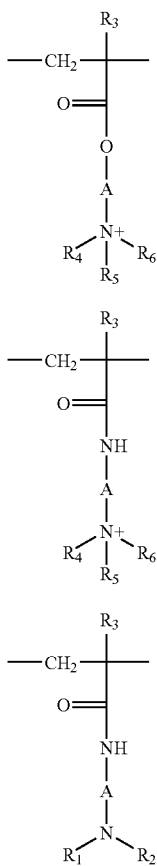

in which:
R$_3$, which may be identical or different, denote a hydrogen atom or a CH$_3$ radical;
A, which may be identical or different, represent a linear or branched alkyl group of 1 to 6 carbon atoms, preferably 2 or 3 carbon atoms, or a hydroxyalkyl group of 1 to 4 carbon atoms;
R$_4$, R$_5$ and R$_6$, which may be identical or different, represent an alkyl group containing from 1 to 18 carbon atoms or a benzyl radical and preferably an alkyl group containing from 1 to 6 carbon atoms;
R$_1$ and R$_2$, which may be identical or different, represent hydrogen or an alkyl group containing from 1 to 6 carbon atoms, and preferably methyl or ethyl;
X denotes an anion derived from an inorganic or organic acid, such as a methosulfate anion or a halide such as chloride or bromide.

The polymers of family (1) can also contain one or more units derived from comonomers which may be chosen from the family of acrylamides, methacrylamides, diacetone acrylamides, acrylamides and methacrylamides substituted on the nitrogen with lower (C$_1$-C$_4$) alkyls, acrylic or methacrylic acids or esters thereof, vinyllactams such as vinylpyrrolidone or vinylcaprolactam, and vinyl esters.

Thus, among these polymers of family (1), mention may be made of:
copolymers of acrylamide and of dimethylaminoethyl methacrylate quaternized with dimethyl sulfate or with a dimethyl halide, such as the product sold under the name Hercofloc® by the company Hercules,
the copolymers of acrylamide and of methacryloyloxyethyltrimethylammonium chloride described, for example, in patent application EP-A-080 976 and sold under the name Bina Quat P 100® by the company Ciba Geigy,
the copolymer of acrylamide and of methacryloyloxyethyltrimethylammonium methosulfate sold under the name Reten® by the company Hercules,
quaternized or non-quaternized vinylpyrrolidone/dialkylaminoalkyl acrylate or methacrylate copolymers, such as the products sold under the name "Gafquat®" by the company ISP, such as, for example, "Gafquat 734" or "Gafquat 755", or alternatively the products known as "Copolymer 845®, 958® and 937®". These polymers are described in detail in French patents 2 077 143 and 2 393 573,
dimethylaminoethyl methacrylate/vinylcaprolactam/vinylpyrrolidone terpolymers, such as the product sold under the name Gaffix VC 713® by the company ISP,
vinylpyrrolidbne/methacrylamidopropyldimethylamine copolymers sold in particular under the name Styleze CC 10® by ISP, and
quaternized vinylpyrrolidone/dimethylaminopropylmethacrylamide copolymers such as the product sold under the name "Gafquat HS 100®" by the company ISP.

(2) The cellulose ether derivatives containing quaternary ammonium groups, described in French patent 1 492 597, and in particular polymers sold under the names "JR®" (JR 400, JR 125 and JR 30M) or "LR®" (LR 400 or LR 30M) by the company Union Carbide Corporation. These polymers are also defined in the CTFA dictionary as quaternary ammoniums of hydroxyethylcellulose that have reacted with an epoxide substituted with a trimethylammonium group.

(3) Cationic cellulose derivatives such as cellulose copolymers or cellulose derivatives grafted with a water-soluble monomer of quaternary ammonium, and described in particular in U.S. Pat. No. 4,131,576, such as hydroxyalkylcelluloses, for instance hydroxymethyl-, hydroxyethyl- or hydroxypropylcelluloses grafted, in particular, with a methacryloylethyltrimethylammonium, methacrylamidopropyltrimethylammonium or dimethyldiallylammonium salt.

The commercial products corresponding to this definition are more particularly the products sold under the names "Celquat L 200®" and "Celquat H 100®" by the company National Starch.

(4) The cationic polysaccharides described more particularly in U.S. Pat. Nos. 3,589,578 and 4,031,307, such as guar gums containing cationic trialkylammonium groups. Guar gums modified with a salt (e.g. chloride) of 2,3-epoxypropyltrimethylammonium are used, for example.

Such products are sold in particular under the trade names Jaguar C13 S®, Jaguar C 15®, Jaguar C 17® or Jaguar C162® by the company Meyhall.

(5) Polymers consisting of piperazinyl units and of divalent alkylene or hydroxyalkylene radicals containing straight or branched chains, optionally interrupted by oxygen, sulfur or nitrogen atoms or by aromatic or heterocyclic rings, as well as the oxidation and/or quaternization products of these polymers. Such polymers are described, in particular, in French patents 2 162 025 and 2 280 361.

(6) Water-soluble polyamino amides prepared in particular by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyamino amide; these polyamino amides can be alkylated or, if they contain one or more tertiary amine functions, they can be quaternized. Such polymers are described, in particular, in French patents 2 252 840 and 2 368 508.

(7) The polyamino amide derivatives resulting from the condensation of polyalkylene polyamines with polycarboxylic acids followed by alkylation with difunctional agents. Mention may be made, for example, of adipic acid/dialkylaminohydroxyalkyldialkylene-triamine polymers in which the alkyl radical contains from 1 to 4 carbon atoms and preferably denotes methyl, ethyl or propyl. Such polymers are described in particular in French patent 1 583 363.

Among these derivatives, mention may be made more particularly of the adipic acid/dimethylaminohydroxypropyl/diethylenetriamine polymers sold under the name "Cartaretine® F, F4 or F8" by the company Sandoz.

(8) The polymers obtained by reaction of a polyalkylene polyamine containing two primary amine groups and at least one secondary amine group with a dicarboxylic acid chosen from diglycolic acid and saturated aliphatic dicarboxylic acids having from 3 to 8 carbon atoms. The molar ratio between the polyalkylene polyamine and the dicarboxylic acid is between 0.8:1 and 1.4:1; the polyamino amide resulting therefrom is reacted with epichlorohydrin in a molar ratio of epichlorohydrin relative to the secondary amine group of the polyamino amide of between 0.5:1 and 1.8:1. Such polymers are described in particular in U.S. Pat. Nos. 3,227,615 and 2,961,347.

Polymers of this type are sold in particular under the name "Hercosett 57®" by the company Hercules Inc. or alternatively under the name "PD 170®" or "Delsette 101®" by the company Hercules in the case of the adipic acid/epoxypropyl/diethylenetriamine copolymer.

(9) Cyclopolymers of dialkyldiallylammonium, such as the homopolymers or copolymers containing, as main constituent of the chain, units corresponding to formula (V):

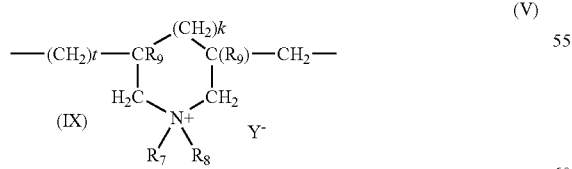

(V)

in which k and t are equal to 0 or 1, the sum k+t being equal to 1;

$R_7$ and $R_8$, which may be identical or different, denote an alkyl group having from 1 to 8 carbon atoms, a $C_1$-$C_5$ hydroxyalkyl group, a $C_1$-$C_4$ amidoalkyl group, or $R_7$ and $R_8$ can denote, together with the nitrogen atom to which they are attached, a piperidyl or morpholinyl group;

$R_9$ denotes a hydrogen atom or a methyl radical;

$R_7$ and $R_8$, independently of each other, preferably denote an alkyl group having from 1 to 4 carbon atoms; $Y^-$ is an anion such as bromide, chloride, acetate, borate, citrate, tartrate, bisulfate, bisulfite, sulfate or phosphate. These polymers are described in particular in French patent 2 080 759 and in its Certificate of Addition 2 190 406.

Among the polymers defined above, mention may be made more particularly of the dimethyldiallylammonium chloride homopolymer sold under the name "Merquat 100®" by the company Calgon (and its homologues of low weight-average molecular mass) and the copolymers of diallyldimethylammonium chloride and of acrylamide, sold under the name "Merquat 550®".

(10) The quaternary diammonium polymer containing repeating units corresponding to the formula:

(VII)

in which formula (VI):

$R_{10}$, $R_{11}$, $R_{12}$ and $R_{13}$, which may be identical or different, represent aliphatic, alicyclic or arylaliphatic radicals containing from 1 to 20 carbon atoms or lower hydroxyalkylaliphatic radicals, or alternatively $R_{10}$, $R_{11}$, $R_{12}$ and $R_{13}$, together or separately, constitute, with the nitrogen atoms to which they are attached, heterocycles optionally containing a second hetero atom other than nitrogen, or alternatively $R_{10}$, $R_{11}$, $R_{12}$ and $R_{13}$ represent a linear or branched $C_1$-$C_6$ alkyl radical substituted with a nitrile, ester, acyl or amide group or a group —CO—O—$R_{14}$-D or —CO—NH—$R_{14}$-D where $R_{14}$ is an alkylene and D is a quaternary ammonium group;

$A_1$ and $B_1$ represent polymethylene groups containing from 2 to 20 carbon atoms which may be linear or branched, saturated or unsaturated, and which may contain, linked to or intercalated in the main chain, one or more aromatic rings or one or more oxygen or sulfur atoms or sulfoxide, sulfone, disulfide, amino, alkylamino, hydroxyl, quaternary ammonium, ureido, amide or ester groups, and $X^-$ denotes an anion derived from an inorganic or organic acid;

$A_1$, $R_{10}$ and $R_{12}$ can form, with the two nitrogen atoms to which they are attached, a piperazine ring; in addition, if $A_1$ denotes a linear or branched, saturated or unsaturated alkylene or hydroxyalkylene radical, $B_1$ can also denote a group —$(CH_2)_n$—CO-D-OC—$(CH_2)_n$— in which D denotes:

a) a glycol residue of formula: —O-Z-O—, where Z denotes a linear or branched hydrocarbon-based radical or a group corresponding to one of the following formulae:

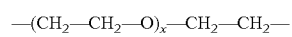

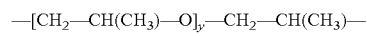

where x and y denote an integer from 1 to 4, representing a defined and unique degree of polymerization or any number from 1 to 4 representing an average degree of polymerization;

b) a bis-secondary diamine residue such as a piperazine derivative;
c) a bis-primary diamine residue of formula: —NH—Y—NH—, where Y denotes a linear or branched hydrocarbon-based radical, or alternatively the divalent radical

—CH$_2$—CH$_2$—S—S—CH$_2$—CH$_2$—;

d) a ureylene group of formula: —NH—CO—NH—.

Preferably, X$^-$ is an anion such as chloride or bromide.

These polymers generally have a number-average molecular mass of between 1000 and 100 000.

Polymers of this type are described in particular in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

It is more particularly possible to use polymers that consist of repeating units corresponding to the following formula (VIII):

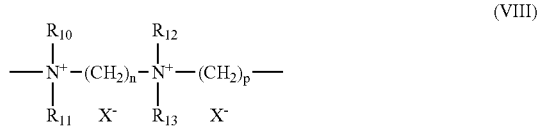

in which $R_{10}$, $R_{11}$, $R_{12}$ and $R_{13}$, which may be identical or different, denote an alkyl or hydroxyalkyl radical containing from 1 to 4 carbon atoms approximately, n and p are integers ranging from 2 to 20 approximately, and X$^-$ is an anion derived from an inorganic or organic acid.

(11) Polyquaternary ammonium polymers consisting of repeating units of formula (IX):

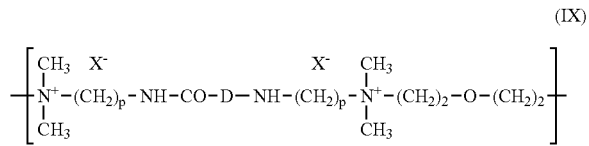

in which p denotes an integer ranging from 1 to 6 approximately, D may be nothing or may represent a group —(CH$_2$)$_r$—CO— in which r denotes a number equal to 4 or 7, X$^-$ is an anion.

Such polymers may be prepared according to the processes described in U.S. Pat. Nos. 4,157,388, 4,702,906 and 4,719,282. They are described in particular in patent application EP-A-122 324.

Among these products, mention may be made, for example, of "Mirapol A 15®", "Mirapol AD1®", "Mirapol AZ1®" and "Mirapol 175®" sold by the company Miranol.

(12) Quaternary polymers of vinylpyrrolidone and of vinylimidazole, such as, for example, the products sold under the names Luviquat FC 905®, FC 550® and FC 370® by the company BASF.

(13) Polyamines such as Polyquart H® sold by Henkel, which is given under the reference name "Polyethylene glycol (15) tallow polyamine" in the CTFA dictionary.

(14) Crosslinked methacryloyloxy(C$_1$-C$_4$)alkyltri(C$_1$-C$_4$)alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, in particular methylenebisacrylamide. A crosslinked acrylamide/methacryloyloxyethyltrimethylammonium chloride copolymer (20/80 by weight) in the form of a dispersion containing 50% by weight of said copolymer in mineral oil can be used more particularly. This dispersion is sold under the name "Salcare® SC 92" by the company Allied Colloids. A crosslinked methacryloyloxyethyltrimethylammonium chloride homopolymer containing about 50% by weight of the homopolymer in mineral oil or in a liquid ester can also be used. These dispersions are sold under the names "Salcare® SC 95" and "Salcare® SC 96" by the company Allied Colloids.

Other cationic polymers which can be used in the context of the invention are polyalkyleneimines, in particular polyethyleneimines, polymers containing vinylpyridine or vinylpyridinium units, condensates of polyamines and of epichlorohydrin, quaternary polyureylenes and chitin derivatives.

Among all the cationic polymers which may be used in the context of the present invention, it is preferred to use the polymers of families (9), (10) and (11) and even more preferably the following:

1/ the dimethyldiallylammonium chloride homopolymer (family 9).

2/ polymers containing the repeating units of formula (VIII) described above (family 10) for which $R_{10}$, $R_{11}$, $R_{12}$ and $R_{13}$ represent a methyl radical, n=3, p=6 and X=Cl, and especially those with a molecular weight, determined by gel permeation chromatography, of between 9500 and 9900 [Polymer W of formula below];

$R_{10}$ and $R_{11}$ represent a methyl radical, $R_{12}$ and $R_{13}$ represent an ethyl radical and n=p=3 and X=Br, and especially those with a molecular weight, determined by gel permeation chromatography, of about 1200 [Polymer U of formula below].

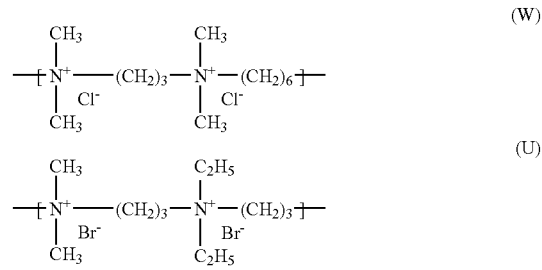

Said polymers containing units (W) and (U) are prepared and described in French patent 2 270 846.

3/ polymers containing units of formula (IX) described above (family 11), for which p is equal to 3, and a) D denotes the value zero, X denotes a chlorine atom, the molecular mass measured by carbon-13 NMR ($^{13}$C NMR) being about 25 500; a polymer of this type is sold by the company Miranol under the name Mirapol-A15®, b) D represents a —(CH$_2$)$_4$—CO— group, X denotes a chlorine atom, the molecular mass measured by carbon-13 NMR ($^{13}$C NMR) being about 5600; a polymer of this type is sold by the company Miranol under the name Mirapol-AD1®, c) D represents a —(CH$_2$)$_7$—CO— group, X denotes a chlorine atom, the molecular mass measured by carbon-13 NMR ($^{13}$C NMR) being about 8100; a polymer of this type is sold by the company Miranol under the name Mirapol-AZ1®, d) a "Block Copolymer" formed from units corresponding to the polymers described in paragraphs a) and b), sold by the company Miranol under the names Mirapol-9® ($^{13}$C NMR molecular mass of about 7800), Mirapol-175® ($^{13}$C NMR molecular mass of about 8000), Mirapol-95® ($^{13}$C NMR molecular mass of about 12 500). Even more particularly preferred according to the invention is the polymer containing units of formula (IX) in which p is equal to 3, D denotes the value zero and X denotes a chlorine atom, the molecular mass measured by carbon-13 NMR ($^{13}$C NMR) being about 25 500 (Mirapol-A15®).

Amiphoteric Polymers

The amphoteric polymers that may be used in accordance with the present invention may be chosen from polymers comprising units K and M randomly distributed in the polymer chain, in which K denotes a unit derived from a monomer comprising at least one basic nitrogen atom and M denotes a unit derived from an acidic monomer comprising one or more carboxylic or sulfonic groups, or alternatively K and M may denote groups derived from zwitterionic carboxybetaine or sulfobetaine monomers;

K and M may also denote a cationic polymer chain comprising primary, secondary, tertiary or quaternary amine groups, in which at least one of the amine groups bears a carboxylic or sulfonic group linked via a hydrocarbon-based radical, or alternatively K and M form part of a chain of a polymer containing an α,β-dicarboxylic ethylene unit in which one of the carboxylic groups has been made to react with a polyamine comprising one or more primary or secondary amine groups.

The amphoteric polymers corresponding to the above definition that are more particularly preferred are chosen from the following polymers:

(1) polymers resulting from the copolymerization of a monomer derived from a vinyl compound bearing a carboxylic group such as, more particularly, acrylic acid, methacrylic acid, maleic acid, α-chloroacrylic acid, and a basic monomer derived from a substituted vinyl compound containing at least one basic atom, such as, more particularly, dialkylaminoalkyl methacrylate and acrylate, dialkylaminoalkylmethacrylamide and -acrylamide. Such compounds are described in U.S. Pat. No. 3,836,537.

Mention may also be made of the sodium acrylate/acrylamidopropyltrimethylammonium chloride copolymer sold under the name Polyquart KE 3033® by the company Henkel.

The vinyl compound may also be a dialkyldiallylammonium salt such as dimethyldiallylammonium chloride. The copolymers of acrylic acid and of the latter monomer are sold under the names Merquat 280® and Merquat 295® by the company Calgon.

(2) Polymers containing units derived from:
a) at least one monomer chosen from acrylamides and methacrylamides substituted on the nitrogen with an alkyl radical,
b) at least one acidic comonomer containing one or more reactive carboxylic groups, and
c) at least one basic comonomer such as esters containing primary, secondary, tertiary and quaternary amine substituents of acrylic and methacrylic acids and the product of quaternization of dimethylaminoethyl methacrylate with dimethyl or diethyl sulfate.

The N-substituted acrylamides or methacrylamides which are more particularly preferred according to the invention are groups in which the alkyl radicals contain from 2 to 12 carbon atoms and more particularly N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers are chosen more particularly from acrylic acid, methacrylic acid, crotonic acid, itaconic acid, maleic acid and fumaric acid and alkyl monoesters, having 1 to 4 carbon atoms, of maleic or fumaric acids or anhydrides.

The preferred basic comonomers are aminoethyl, butylaminoethyl, N,N'-dimethylaminoethyl and N-tert-butylaminoethyl methacrylates.

The copolymers whose CTFA (4th edition, 1991) name is octylacrylamide/acrylates/butylaminoethyl methacrylate copolymer such as the products sold under the name Amphomer® or Lovocryl 47® by the company National Starch are particularly used.

(3) Crosslinked and alkylated polyamino amides partially or totally derived from polyamino amides of general formula:

$$\text{-[CO-R}_{19}\text{-CO-Z]-} \quad (X)$$

in which R$_{19}$ represents a divalent radical derived from a saturated dicarboxylic acid, a mono- or dicarboxylic aliphatic acid containing an ethylenic double bond, an ester of a lower alkanol, having 1 to 6 carbon atoms, of these acids or a radical derived from the addition of any one of said acids to a bis(primary) or bis(secondary) amine, and Z denotes a bis(primary), mono- or bis(secondary) polyalkylene-polyamine radical and preferably represents:

a) in proportions of from 60 to 100 mol %, the radical

where x=2 and p=2 or 3, or alternatively x=3 and p=2 this radical being derived from diethylenetriamine, from triethylenetetraamine or from dipropylenetriamine;

b) in proportions of from 0 to 40 mol %, the radical (XI) above in which x=2 and p=1 and which is derived from ethylenediamine, or the radical derived from piperazine:

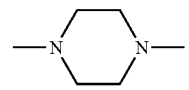

c) in proportions of from 0 to 20 mol %, the —NH—(CH$_2$)$_6$—NH— radical derived from hexamethylenediamine, these polyamino amines being crosslinked by addition of a difunctional crosslinking agent chosen from epihalohydrins, diepoxides, dianhydrides and bis-unsaturated derivatives, using from 0.025 to 0.35 mol of crosslinking agent per amine group of the polyamino amide and alkylated by the action of acrylic acid, chloroacetic acid or an alkane sultone, or salts thereof.

The saturated carboxylic acids are preferably chosen from acids having 6 to 10 carbon atoms, such as adipic acid, 2,2,4-trimethyladipic acid and 2,4,4-trimethyladipic acid, terephthalic acid and acids containing an ethylenic double bond such as, for example, acrylic acid, methacrylic acid and itaconic acid.

The alkane sultones used in the alkylation are preferably propane sultone or butane sultone, and the salts of the alkylating agents are preferably the sodium or potassium salts.

(4) Polymers containing zwitterionic units of formula:

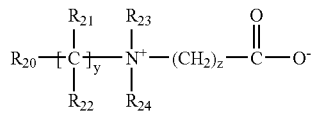
(XII)

in which $R_{20}$ denotes a polymerizable unsaturated group such as an acrylate, methacrylate, acrylamide or methacrylamide group, y and z represent an integer from 1 to 3, $R_{21}$ and $R_{22}$ represent a hydrogen atom, methyl, ethyl or propyl, $R_{23}$ and $R_{24}$ represent a hydrogen atom or an alkyl radical such that the sum of the carbon atoms in $R_{23}$ and $R_{24}$ does not exceed 10.

The polymers comprising such units can also contain units derived from non-zwitterionic monomers such as dimethyl or diethylaminoethyl acrylate or methacrylate or alkyl acrylates or methacrylates, acrylamides or methacrylamides or vinyl acetate.

By way of example, mention may be made of the copolymer of butyl methacrylate/dimethyl carboxymethylammonio ethyl methacrylate such as the product sold under the name Diaformer Z301® by the company Sandoz.

(5) Polymers derived from chitosan described especially in French patent 2 137 684 or U.S. Pat. No. 3,879,376, comprising monomer units corresponding to formulae (XIII), (XIV) and (XV) below combined in their chain:

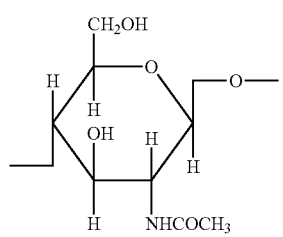
(XIII)

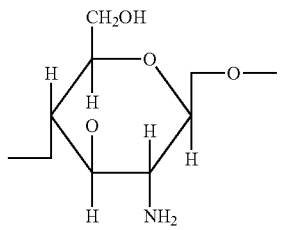
(XIV)

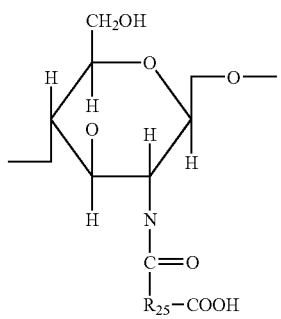
(XV)

the unit (XIII) being present in proportions of between 0 and 30%, the unit (XIV) in proportions of between 5 and 50% and the unit (XV) in proportions of between 30 and 90%, it being understood that, in this unit (XV), $R_{25}$ represents a radical of formula:

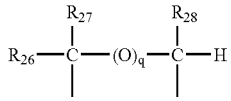

in which q denotes zero or 1;
if q=0, $R_{26}$, $R_{27}$ and $R_{28}$, which may be identical or different, each represent a hydrogen atom, a methyl, hydroxyl, acetoxy or amino residue, a monoalkylamine residue or a dialkylamine residue which are optionally interrupted by one or more nitrogen atoms and/or optionally substituted with one or more amine, hydroxyl, carboxyl, alkylthio or sulfonic groups, an alkylthio residue in which the alkyl group bears an amino residue, at least one of the radicals $R_{26}$, $R_{27}$ and $R_{28}$ being, in this case, a hydrogen atom;
or, if q=1, $R_{26}$, $R_{27}$ and $R_{28}$ each represent a hydrogen atom, as well as the salts formed by these compounds with bases or acids.

(6) Polymers derived from the N-carboxyalkylation of chitosan, such as N-carboxymethylchitosan or N-carboxybutylchitosan sold under the name "Evalsan®" by the company Jan Dekker.

(7) Polymers corresponding to the general formula (XVI) as described, for example, in French patent 1 400 366:

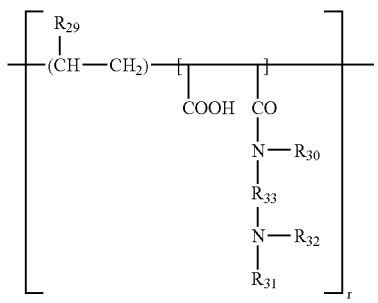

(XVI)

in which $R_{29}$ represents a hydrogen atom, a $CH_3O$, $CH_3CH_2O$ or phenyl radical, $R_{30}$ denotes hydrogen or a lower alkyl radical such as methyl or ethyl, $R_{31}$ denotes hydrogen or a lower alkyl radical such as methyl or ethyl, $R_{32}$ denotes a lower alkyl radical such as methyl or ethyl or a radical corresponding to the formula: —$R_{33}$—$N(R_{31})_2$, $R_{33}$ representing a —$CH_2$—$CH_2$—, —$CH_2$—$CH_2$—$CH_2$— or —$CH_2$—$CH(CH_3)$— group, $R_{31}$, having the meanings mentioned above, as well as the higher homologues of these radicals and containing up to 6 carbon atoms, r is such that the molecular weight is between 500 and 6 000 000 and preferably between 1000 and 1 000 000.

(8) Amphoteric polymers of the type -D-X-D-X— chosen from:

a) polymers obtained by the action of chloroacetic acid or sodium chloroacetate on compounds containing at least one unit of formula:

-D-X-D-X-D- (XVII)

where D denotes a radical

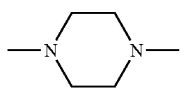

and X denotes the symbol E or E', E or E', which may be identical or different, denotes a divalent radical which is an alkylene radical with a straight or branched chain containing up to 7 carbon atoms in the main chain, which is unsubstituted or substituted with hydroxyl groups and which can contain, in addition to the oxygen, nitrogen and sulfur atoms, 1 to 3 aromatic and/or heterocyclic rings; the oxygen, nitrogen and sulfur atoms being present in the form of ether, thioether, sulfoxide, sulfone, sulfonium, alkylamine or alkenylamine groups, hydroxyl, benzylamine, amine oxide, quaternary ammonium, amide, imide, alcohol, ester and/or urethane groups;

b) polymers of formula:

-D-X-D-X— (XVIII)

where D denotes a radical

and X denotes the symbol E or E' and at least once E'; E having the meaning given above and E' being a divalent radical which is an alkylene radical with a straight or branched chain having up to 7 carbon atoms in the main chain, which is unsubstituted or substituted with one or more hydroxyl radicals and containing one or more nitrogen atoms, the nitrogen atom being substituted with an alkyl chain which is optionally interrupted by an oxygen atom and necessarily containing one or more carboxyl functions or one or more hydroxyl functions and betainized by reaction with chloroacetic acid or sodium chloroacetate.

(9) ($C_1$-$C_5$)alkyl vinyl ether/maleic anhydride copolymers partially modified by semiamidation with an N,N-dialkylaminoalkylamine such as N,N-dimethylamino-propylamine or by semiesterification with an N,N-dialkanolamine. These copolymers can also contain other vinyl comonomers such as vinylcaprolactam.

Among all the amphoteric polymers that may be used in the context of the present invention, it is preferred to use the polymers of family (1) and in particular copolymers of acrylic acid and of dimethyldiallylammonium chloride.

According to the invention, the cationic or amphoteric polymer(s) other than the cationic or amphoteric associative polymers and than the polymers containing (i) acrylamide, (ii) dialkyldiallylammonium halide and (iii) acrylic acid units according to the invention may represent from about 0.01% to 10% by weight, preferably 0.05% to 5% by weight and even more preferably 0.1% to 3% by weight relative to the total weight of the composition.

The dye composition may also contain an effective amount of other agents, known previously elsewhere in oxidation dyeing, such as various common adjuvants, for instance sequestering agents such as EDTA and etidronic acid, UV screening agents, waxes, volatile or non-volatile, cyclic or linear or branched silicones, which are optionally organomodified (in particular with amine groups), preserving agents, ceramides, pseudoceramides, plant, mineral or synthetic oils, vitamins or provitamins, for instance panthenol, opacifiers, etc.

The dye composition may also comprise other rheology modifiers such as cellulose-based thickeners (hydroxyethylcellulose, hydroxypropylcellulose, carboxymethylcellulose, etc.), guar gum and its derivatives (hydroxypropylguar, etc.), gums of microbial origin (xanthan gum, scleroglucan gum, etc.), synthetic thickeners such as crosslinked homopolymers of acrylic acid or of acrylamidopropanesulfonic acid.

These additional thickeners may represent from 0.01% to 10% by weight relative to the total weight of the composition.

Said composition may also contain reducing agents or antioxidants. These agents may be chosen in particular from sodium metabisulfite, thioglycolic acid, thiolactic acid, sodium bisulfite, dehydroascorbic acid, hydroquinone, 2-methylhydroquinone, tert-butylhydroquinone and homogentisic acid, and, in this case, they are generally present in amounts ranging from about 0.05% to 3% by weight relative to the total weight of the composition.

Needless to say, a person skilled in the art will take care to select the optional additional compound(s) mentioned above such that the advantageous properties intrinsically associated with the dye composition according to the invention are not, or are not substantially, adversely affected by the envisaged addition(s).

In the ready-to-use composition or in the oxidizing composition, the oxidizing agent is preferably chosen from urea peroxide, alkali metal bromates or ferricyanides, and persalts such as perborates and persulfates. It is particularly preferred to use hydrogen peroxide. This oxidizing agent advantageously consists of an aqueous hydrogen peroxide solution whose titer may range, more particularly, from about 1 to 40 volumes and even more preferably from about 5 to 40 volumes.

Oxidizing agents that may also be used are one or more redox enzymes such as 4-electron oxidoreductases (such as laccases), peroxidases and 2-electron oxidoreductases (such as uricase), where appropriate in the presence of their respective donor or co-factor.

The pH of the ready-to-use composition applied to the keratin fibers [composition resulting from mixing together the dye composition and the oxidizing composition] is generally between 3 and 12. It is preferably between 8.5 and 11, and may be adjusted to the desired value using acidifying or basifying agents that are well known in the prior art in the dyeing of keratin fibers.

Among the basifying agents which may be mentioned, for example, are aqueous ammonia, alkali metal carbonates, alkanolamines such as monoethanolamine, diethanolamine and triethanolamine and derivatives thereof, sodium hydroxide, potassium hydroxide and the compounds of the following formula (VI):

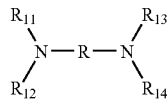
(VI)

in which R is a propylene residue optionally substituted with a hydroxyl group or a $C_1$-$C_4$ alkyl radical; $R_{11}$, $R_{12}$, $R_{13}$ and $R_{14}$, which may be identical or different, represent a hydrogen atom, a $C_1$-$C_4$ alkyl radical or a $C_1$-$C_4$ hydroxyalkyl radical.

The acidifying agents are conventionally, for example, mineral or organic acids, for instance hydrochloric acid, orthophosphoric acid, carboxylic acids, for instance tartaric acid, citric acid or lactic acid, or sulfonic acids.

The dyeing process according to the invention preferably consists in applying a mixture, prepared extemporaneously at the time of use (ready-to-use composition) from the dye composition and the oxidizing composition described above, to wet or dry keratin fibers, and in leaving the composition to act for an exposure time preferably ranging from 1 to 60 minutes approximately, and more preferably from 5 to 45 minutes approximately, in rinsing the fibers and then in optionally washing them with shampoo, then rinsing them again and drying them.

Concrete examples illustrating the invention will now be given without, however, being limiting in nature.

EXAMPLE 1

The cationic associative polyurethane below was synthesized:

| Reagents: | |
|---|---|
| polyethylene oxide (PEG) ($M_n$ 10 000): | 0.010 mol |
| methylenedicyclohexyl diisocyanate: | 0.018 mol |
| N,N-dimethylethanolamine: | 0.020 mol |
| stearyl bromide: | 0.024 mol |
| tin octanoate (catalyst): | 0.2% |

0.010 mol (100 g) of poly(ethylene oxide) (PEG) with a number-average mass of 10 000 was dissolved in 105 g of THF containing 0.2% of tin octanoate (catalyst), followed by dropwise addition of 0.018 mol (4.71 g) of methylenedicyclohexyl diisocyanate. The reaction medium was heated for 15 hours at the reflux temperature of the THF, adding 100 ml of THF after 6 hours. During the reaction, partial disappearance of the NCO band of the isocyanate was observed by FTIR and appearance of the CO and NH bands for the amide bonds formed was observed. The medium was very viscous and transparent.

0.020 mol (1.78 g) of N,N-dimethylethanolamine was then added and the reaction was continued for 4 hours at the reflux temperature of the THF until the NCO band and the OH band of the alcohol had completely disappeared.

For the quaternization, 0.024 mol (8 g) of stearyl bromide, i.e. a 20 mol % excess relative to the N,N-dimethylethanolamine, was added to the reaction mixture, followed by addition of 100 g of THF to fluidize the very viscous reaction medium. Heating at the reflux temperature of the THF was continued for a further 36 hours.

The polymer obtained was precipitated in petroleum ether, filtered off and dried under vacuum at 40° C. for 24 hours. A crumbly white powder was thus obtained.

A number-average mass of 70 000 and a weight-average mass of 115 000, which corresponded to a polydispersity index of 1.65, were measured by gel permeation chromatography in aqueous medium (calibration with polystyrene).

EXAMPLE 2

The oxidation dye composition below, in accordance with the invention, was prepared:

(expressed in grams)

| Dye composition: | |
|---|---|
| Mixture of linear C18 to C24 alcohols [C18/C20/C22/C24: 7/58/30/6 - alcohol content >95%] | 3 |
| Mixture of oxyethylenated (30 EO) linear C18 to C24 alcohols [C18/C20/C22/C24: 7/58/30/6 - alcohol content >95%] | 1 |
| Oxyethylenated (2 EO) stearyl alcohol | 4.5 |
| Oxyethylenated (21 EO) stearyl alcohol | 1.75 |
| Oleic acid | 2.6 |
| Crosslinked polyacrylic acid (Carbopol 980 from Goodrich) | 0.6 |
| Cationic associative polyurethane of example 1 | 3.5 |
| | AM* |

-continued

| | |
|---|---|
| Coconut acid monoisopropanolamide | 3 |
| Merquat Plus 3330 sold by Calgon, as an aqueous solution containing 10% AM* | 1.2 AM* |
| Propylene glycol | 6 |
| Sodium metabisulfite | 0.71 |
| EDTA (ethylenediaminetetraacetic acid) | 0.2 |
| tert-Butyl hydroquinone | 0.3 |
| 1,4-Diaminobenzene | 0.5 |
| para-Aminophenol | 0.1 |
| 1,3-Dihydroxybenzene | 0.6 |
| 1-Hydroxy-3-aminobenzene | 0.1 |
| 1-β-Hydroxyethyloxy-2,4-diaminobenzene dihydrochloride | 0.04 |
| Monoethanolamine | 1 |
| Aqueous ammonia containing 20% $NH_3$ | 11 |
| Fragrance | qs |
| Demineralized water qs | 100 |
| Oxidizing composition: | |
| Fatty alcohol | 2.3 |
| Oxyethylenated fatty alcohol | 0.6 |
| Fatty amide | 0.9 |
| Glycerol | 0.5 |
| Hydrogen peroxide | 7.5 |
| Fragrance | qs |
| Demineralized water qs | 100 |

Said dye composition was mixed, at the time of use, in a plastic bowl, with the oxidizing composition given above, at a rate of 1 part of dye composition per 1.5 parts of oxidizing composition.

The mixture obtained was applied to locks of natural hair containing 90% white hairs and was left to act for 30 minutes.

The locks were then rinsed with water, washed with standard shampoo, rinsed again with water and then dried and disentangled.

The hair was dyed a dark blonde shade, with good staying power, and the cosmetic condition of the hair was improved.

EXAMPLE 3

The oxidation dye composition below, in accordance with the invention, was prepared:

(expressed in grams)

| | |
|---|---|
| Dye composition: | |
| Mixture of linear C18 to C24 alcohols [C18/C20/C22/C24: 7/58/30/6 - alcohol content >95%] | 3 |
| Mixture of oxyethylenated (30 EO) linear C18 to C24 alcohols [C18/C20/C22/C24: 7/58/30/6 - alcohol content >95%] | 1 |
| Oxyethylenated (2 EO) stearyl alcohol | 4.5 |
| Oxyethylenated (21 EO) stearyl alcohol | 1.75 |
| Oleic acid | 2.6 |
| Crosslinked polyacrylic acid (Carbopol 980 from Goodrich) | 0.6 |
| Aculyn 44 or Aculyn 46 sold by Rohm & Haas | 4 |
| Coconut acid monoisopropanolamide | 3 |
| Merquat Plus 3330 sold by Calgon, as an aqueous solution containin 10% AM* | 1.2 AM* |
| Propylene glycol | 6 |
| Sodium metabisulfite | 0.71 |
| EDTA (ethylenediaminetetraacetic acid) | 0.2 |
| tert-Butyl hydroquinone | 0.3 |
| 1,4-Diaminobenzene | 0.5 |
| para-Aminophenol | 0.1 |
| 1,3-Dihydroxybenzene | 0.6 |
| 1-Hydroxy-3-aminobenzene | 0.1 |
| 1-μ-Hydroxyethyloxy-2,4-diaminobenzene dihydrochionde | 0.04 |
| Monoethanolamine | 1 |
| Aqueous ammonia containing 20% $NH_3$ | 11 |

-continued

| | | |
|---|---|---|
| Fragrance | qs | |
| Demineralized water | qs | 100 |
| Oxidizing composition: | | |
| Fatty alcohol | | 2.3 |
| Oxyethylenated fatty alcohol | | 0.6 |
| Fatty amide | | 0.9 |
| Glycerol | | 0.5 |
| Hydrogen peroxide | | 7.5 |
| Fragrance | | qs |
| Demineralized water | qs | 100 |

AM* denotes Active Material

Said dye composition was mixed, at the time of use, in a plastic bowl, with the oxidizing composition given above, at a rate of 1 part of dye composition per 1.5 parts of oxidizing composition.

The mixture obtained was applied to locks of natural hair containing 90% white hairs and was left to act for 30 minutes.

The locks were then rinsed with water, washed with standard shampoo, rinsed again with water and then dried and disentangled.

The hair was dyed a dark blonde shade, with good staying power, and the cosmetic condition of the hair was improved.

EXAMPLE 4

The composition of example 3 was reproduced, replacing the 4 grams of Aculyn 44® or of Aculyn 46® with 3.8 g AM of Pemulen TR1® sold by Goodrich. By following the same protocol as in example 3, the oxidation dye composition obtained gave identical performance qualities in terms of cosmetic condition of the hair and dyeing power.

EXAMPLE 5

The composition of example 3 was reproduced, replacing the 4 grams of Aculyn 44® or of Aculyn 46® with 3.8 g AM of Quatrisoft LM200® sold by Amerchol. By following the same protocol as in exampel 3, the oxidation dye composition obtained gave identical performance qualities in terms of cosmetic condition of the hair and dyeing power.

The invention claimed is:

1. A composition for dyeing keratin fibers, comprising, in a medium suitable for dyeing,
   at least one dye,
   at least one associative polymer chosen from cationic, amphoteric, non-ionic, and anionic associative polymers, wherein the anionic associative polymers are chosen from:
   (I) anionic associative polymers having at least one hydrophilic unit and at least one fatty-chain allyl ether unit;
   (II) anionic associative polymers having at least one hydrophilic unit of unsaturated olefinic carboxylic acid type, and at least one hydrophobic unit of ($C_{10}$-$C_{30}$)alkyl ester of unsaturated carboxylic acid type chosen from acrylic acid, methacrylic acid, and ethacrylic acid;
   (III) maleic anhydride/α-olefin and $C_{30}$-$C_{38}$/alkyl maleate terpolymers;
   (IV) acrylic terpolymers comprising;
      (a) about 20% to 70% by weight of an α-β-monoethlyene unsaturated carboxylic acid;
      (b) about 20% to 80% by weight of a non-surfactant α-β-monoethlyene unsaturated monomer different from (a); and (c) about 0.5% to 60% by weight of a non-ionic monourethane that is the reaction product of a monohydric surfactant with a monoethylene unsaturated monoisocyanate; and (V) a copolymer comprising an α-β-monoethlyene unsaturated carboxylic acid and an α-β-monoethlyene unsaturated carboxylic acid ester and an oxyalkylenated fatty alcohol, said copolymer being a methacrylic acid/ethyl acrylate/stearyl methacrylate oxyalkylenated terpolymer, and at least one polymer comprising (i) acrylamide, (ii) dialkyldiallylammonium halide, and (iii) vinylcarboxylic acid units, said polymer being an acrylamide/dimethyldiallylammonium chloride/acrylic acid terpolymer.

2. The composition according to claim 1, wherein the keratin fibers are human keratin fibers.

3. The composition according to claim 2, wherein the human keratin fibers are hair.

4. The composition according to claim 1, wherein the at least one dye is chosen from direct dyes and oxidation dyes.

5. The composition according to claim 4, wherein the oxidation dyes are chosen from oxidation bases and couplers.

6. The composition according to claim 5, wherein the oxidation bases are chosen from ortho- and para-phenylenediamines, double bases, ortho- and para-aminophenols, and heterocyclic bases, and the acid addition salts thereof.

7. The composition according to claim 6, wherein the oxidation bases are present in an amount ranging from 0.0005% to 12% by weight, relative to the total weight of the composition.

8. The composition according to claim 5, wherein the couplers are chosen from meta-aminophenols, meta-phenylenediamines, meta-diphenols, naphthols, and heterocyclic couplers, and the acid addition salts thereof.

9. The composition according to claim 8, wherein the couplers are present in an amount ranging from 0.0001% to 10% by weight, relative to the total weight of the composition.

10. The composition according to claim 6, wherein the acid addition salts of the oxidation bases are chosen from hydrochlorides, hydrobromides, sulfates, tartrates, lactates, and acetates.

11. The composition according to claim 8, wherein the acid addition salts of the couplers are chosen from hydrochlorides, hydrobromides, sulfates, tartrates, lactates, and acetates.

12. The composition according to claim 5, further comprising at least one oxidizing agent.

13. The composition according to claim 12, further comprising at least one direct dye present in an amount ranging from 0.001% to 20% by weight, relative to the total weight of the composition.

14. The composition according to claim 1, wherein the at least one polymer comprising (i) acrylamide, (ii) dialkyldiallylammonium halide, and (iii) vinylcarboxylic acid units is present in an amount ranging from 0.1% to 10% by weight, relative to the total weight of the composition.

15. The composition according to claim 14, wherein the at least one polymer comprising (i) acrylamide, (ii) dialkyldiallylammonium halide, and (iii) vinylcarboxylic acid units is present in an amount ranging from 0.5% to 5% by weight, relative to the total weight of the composition.

16. The composition according to claim 15, wherein the at least one polymer comprising (i) acrylamide, (ii) dialkyldiallylammonium halide, and (iii) vinylcarboxylic acid units is present in an amount ranging from 1% to 3% by weight, relative to the total weight of the composition.

17. The composition according to claim 1, wherein the at least one associative polymer is chosen from anionic, nonionic, cationic and amphoteric polymers.

18. The composition according to claim 17, wherein the at least one associative polymer is nonionic and chosen from polyurethane polyethers.

19. The composition according to claim 18, wherein the polyurethane polyethers are chosen from polycondensates of (i) polyethylene glycol comprising 150 or 180 mol of ethylene oxide, (ii) stearyl alcohol, and (iii) at least one diisocyanate.

20. The composition according to claim 19, wherein the polyurethane polyethers are chosen from polycondensates of (i) polyethylene glycol comprising 150 or 180 mol of ethylene oxide, (ii) stearyl alcohol and (iii) methylenebis(4-cyclohexyl isocyanate) (SMDI) in an amount of 15% by weight, in a matrix of 4% by weight of maltodextrin and 81% by weight of water, wherein the weight percentages are relative to the total weight of the matrix.

21. The composition according to claim 18, wherein the polyurethane polyethers are chosen from polycondensates of (i) polyethylene glycol comprising 150 or 180 mol of ethylene oxide, (ii) decyl alcohol, and (iii) at least one diisocyanate.

22. The composition according to claim 21, wherein the polyurethane polyethers are chosen from polycondensates of (i) polyethylene glycol comprising 150 or 180 mol of ethylene oxide, (ii) decyl alcohol, and (iii) methylenebis(4-cyclohexyl isocyanate) (SMDI) in an amount of 35% by weight, in a mixture of 39% by weight of propylene glycol and 26% by weight of water, wherein the weight percentages are relative to the total weight of the mixture.

23. The composition according to claim 1, wherein the at least one associative polymer is present in an amount ranging from 0.1% to 10% by weight, relative to the total weight of the composition.

24. The composition according to claim 23, wherein the at least one associative polymer is present in an amount ranging from 0.5% to 5% by weight, relative to the total weight of the composition.

25. The composition according to claim 24, wherein the at least one associative polymer is present in an amount ranging from 1% to 3% by weight, relative to the total weight of the composition.

26. The composition according to claim 1, further comprising at least one additional polymer chosen from cationic and amphoteric polymers other than the at least one associative polymer and the at least one polymer comprising (i) acrylamide, (ii) dialkyldiallylammonium halide, and (iii) vinylcarboxylic acid units.

27. The composition according to claim 26, wherein the at least one additional polymer is chosen from:
dimethyldiallylammonium chloride homopolymers;
polymers comprising repeating units chosen from units of formula (W) and (U) below:

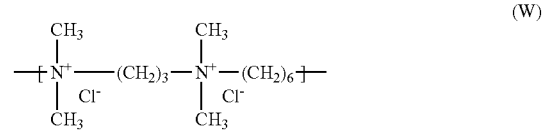

-continued

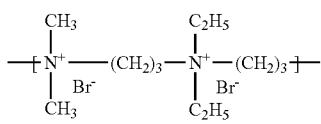
(U)

polymers comprising units of formula (IX) below:

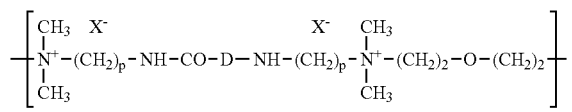
(IX)

wherein p is equal to 3, and
a) D is equal to zero, X is a chlorine atom,
b) D is a —$(CH_2)_4$—CO— group, X is a chlorine atom, or
c) D is a —$(CH_2)_7$—CO— group, X is a chlorine atom,
block copolymers formed from units corresponding to the units of formula (IX)
wherein p is equal to 3, and
a) D is equal to zero, X is a chlorine atom, and
b) D is a —$(CH_2)_4$—CO— group, X is a chlorine atom; and
copolymers of acrylic acid and of dimethyldiallylammonium chloride.

28. The composition according to claim 26, wherein the at least one additional polymer is present in an amount ranging from 0.01% to 10% by weight, relative to the total weight of the composition.

29. The composition according to claim 1, further comprising at least one surfactant chosen from anionic, cationic, nonionic, amphoteric and zwitterionic surfactants.

30. The composition according to claim 29, wherein the at least one surfactant chosen from anionic, cationic, nonionic, amphoteric and zwitterionic surfactants is present in an amount of at least 0.01% by weight, relative to the total weight of the composition.

31. The composition according to claim 29, wherein the at least one surfactant is chosen from nonionic surfactants.

32. The composition according to claim 12, wherein the pH of the composition ranges from 3 to 12.

33. The composition according to claim 32, wherein the pH of the composition ranges from 8.5 to 11.

34. The composition according to claim 12, wherein the at least one oxidizing agent is chosen from hydrogen peroxide, urea peroxide, alkali metal bromates and ferricyanides, persalts, and redox enzymes optionally with the respective donor or co-factor thereof.

35. The composition according to claim 34, wherein the at least one oxidizing agent is hydrogen peroxide.

36. The composition according to claim 35, wherein the at least one oxidizing agent is an aqueous hydrogen peroxide solution whose titer ranges from 1 to 40 volumes.

37. A process for dyeing keratin fibers comprising:
applying to the keratin fibers a dye composition comprising, in a medium suitable for dyeing, at least one dye chosen from direct dyes and oxidation dyes, and
applying to the keratin fibers an oxidizing composition comprising at least one oxidizing agent,
wherein:
a color is developed at alkaline, neutral or acidic pH;
the dye composition is mixed with the oxidizing composition at the time of use or the oxidizing composition is applied sequentially without intermediate rinsing; and
at least one of the dye composition and the oxidizing composition further comprises at least one associative polymer and at least one polymer comprising (i) acrylamide, (ii) dialkyldiallylammonium halide, and (iii) vinylcarboxylic acid units.

38. The process according to claim 37, wherein the keratin fibers are human keratin fibers.

39. The process according to claim 38, wherein the human keratin fibers are hair.

40. The process according to claim 37, wherein the at least one associative polymer and the at least one polymer comprising (i) acrylamide, (ii) dialkyldiallylammonium halide, and (iii) vinylcarboxylic acid units are present in the dye composition.

41. The process according to claim 37, comprising:
applying to wet or dry keratin fibers a ready-to-use composition prepared extemporaneously at the time of use comprising the dye composition and the oxidizing composition,
leaving the ready-to-use composition on the keratin fibers to act for an exposure time ranging from 1 to 60 minutes, and
rinsing the keratin fibers, optionally washing the keratin fibers with shampoo, further rinsing the keratin fibers, and drying the keratin fibers.

42. The process according to claim 41, wherein the exposure time for the ready-to-use composition on the keratin fibers to act ranges from 5 to 45 minutes.

43. A multi-compartment device for dyeing keratin fibers, comprising at least one compartment comprising a dye composition comprising, in a medium suitable for dyeing, at least one dye chosen from direct dyes and oxidation dyes, and at least one other compartment comprising an oxidizing composition comprising, in a medium suitable for dyeing, at least one oxidizing agent, wherein at least one of the dye composition and the oxidizing composition further comprises at least one associative polymer and at least one polymer comprising (i) acrylamide, (ii) dialkyldiallylammonium halide, and (iii) vinylcarboxylic acid units.

44. The device according to claim 43, wherein the keratin fibers are human keratin fibers.

45. The device according to claim 44, wherein the human keratin fibers are hair.

* * * * *